United States Patent
Lang et al.

(10) Patent No.: US 9,585,922 B2
(45) Date of Patent: Mar. 7, 2017

(54) LACTIC ACID BACTERIA THAT CO-AGGREGATE WITH PATHOGENIC BACTERIA

(75) Inventors: Christine Lang, Berlin (DE); Andreas Raab, Berlin (DE); Patrick Golletz, Berlin (DE)

(73) Assignee: ORGANOBALANCE MEDICAL AG, Berlin (DE)

( * ) Notice: Subject to any disclaimer, the term of this patent is extended or adjusted under 35 U.S.C. 154(b) by 151 days.

(21) Appl. No.: 14/115,671

(22) PCT Filed: May 7, 2012

(86) PCT No.: PCT/DE2012/100129
§ 371 (c)(1),
(2), (4) Date: Nov. 5, 2013

(87) PCT Pub. No.: WO2012/152270
PCT Pub. Date: Nov. 15, 2012

(65) Prior Publication Data
US 2014/0186409 A1    Jul. 3, 2014

(30) Foreign Application Priority Data
May 6, 2011   (DE) .................. 10 2011 101 134

(51) Int. Cl.
| | | |
|---|---|---|
| A61K 35/74 | (2015.01) | |
| A61K 35/744 | (2015.01) | |
| A61K 35/747 | (2015.01) | |
| A61K 8/99 | (2006.01) | |
| C12N 1/20 | (2006.01) | |
| C12R 1/225 | (2006.01) | |
| A61Q 17/00 | (2006.01) | |
| A61Q 19/10 | (2006.01) | |
| C11D 3/38 | (2006.01) | |
| C12Q 1/04 | (2006.01) | |

(52) U.S. Cl.
CPC .......... *A61K 35/747* (2013.01); *A23L 33/135* (2016.08); *A61K 8/99* (2013.01); *A61K 35/74* (2013.01); *A61K 35/744* (2013.01); *A61Q 17/005* (2013.01); *A61Q 19/10* (2013.01); *C11D 3/381* (2013.01); *C12N 1/20* (2013.01); *C12Q 1/04* (2013.01); *C12R 1/225* (2013.01); *A23V 2002/00* (2013.01)

(58) Field of Classification Search
None
See application file for complete search history.

(56) References Cited

U.S. PATENT DOCUMENTS

| | | |
|---|---|---|
| 6,790,434 B2 | 9/2004 | Borchert et al. |
| 7,846,711 B2 | 12/2010 | Boettner et al. |
| 2006/0002910 A1* | 1/2006 | Baur .................. A61K 8/99 424/93.45 |

FOREIGN PATENT DOCUMENTS

| | | |
|---|---|---|
| EP | 1 634 948 A1 | 3/2006 |
| WO | 9725865 A1 | 7/1997 |
| WO | 2007/073709 A1 | 7/2007 |
| WO | 2008/064893 A1 | 6/2008 |

OTHER PUBLICATIONS

N.A. Soleimani et al.: "Antagonistic activity of probiotic lactobacilli against *Staphylococcus aureus* isolated from bovine mastitis", in: African Journal of Microbiology Research, vol. 4, No. 20, Oct. 18, 2010, pp. 2169-2173.
Lang C et al: "Specific Lactobacillus/Mutans Streptococcus co-aggregation", in: Journal of Dental Research, International & American Association for Dental Research, vol. 89, No. 2, Feb. 1, 2010, pp. 175-179.
Eva M Soederling et al: "Probiotic Lactobacilli Interfere with Biofilm Formation in Vitro", in: Current Microbiology, Springer-Verlag, NE, vol. 62, No. 2, 2011, pp. 618-622.
Jamalifar H. et al.: "Antimicrobial activity of different Lactobacillus species against multidrug resistant clinical isolates of Pseudomonas aeruginosa", in: Iranian Journal of Microbiology, vol. 3, No. 1, Mar. 1, 2011, pp. 21-25.
Jessica A. Younes et al: "Adhesion Forces and Coaggregation between Vaginal Staphylococci and Lactobacilli'", in: Plos ONE, vol. 7, No. 5, May 18, 2012, pp. e36917-e36917.

* cited by examiner

*Primary Examiner* — Kevin S Orwig
(74) *Attorney, Agent, or Firm* — Joyce von Natzmer; Agris & von Natzmer LLP

(57) ABSTRACT

The invention relates to a microorganism, of the order of lactic acid bacteria or analog, fragment, derivative, mutant or combination thereof. Said microorganism, or analog, fragment, derivative, mutants or combinations thereof can be co-aggregated with at least *Staphylococcus aureus* or *Pseudomonas aeruginosa*.

11 Claims, 7 Drawing Sheets

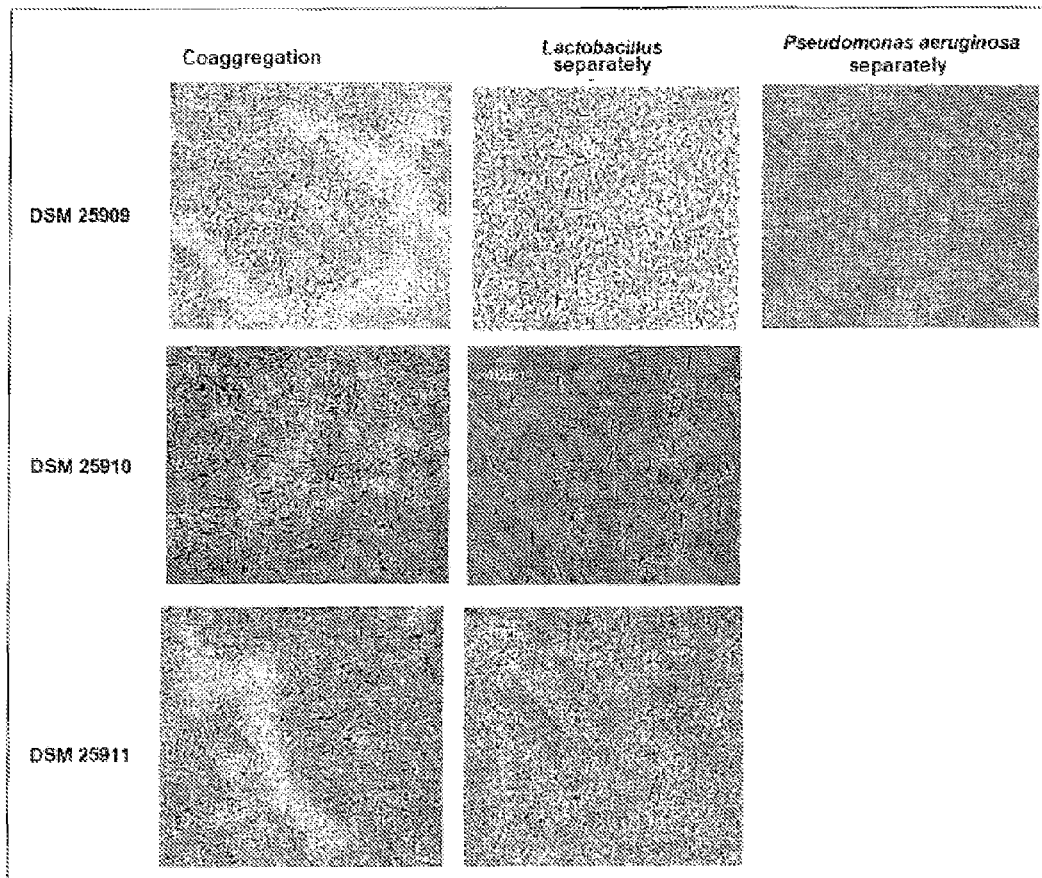
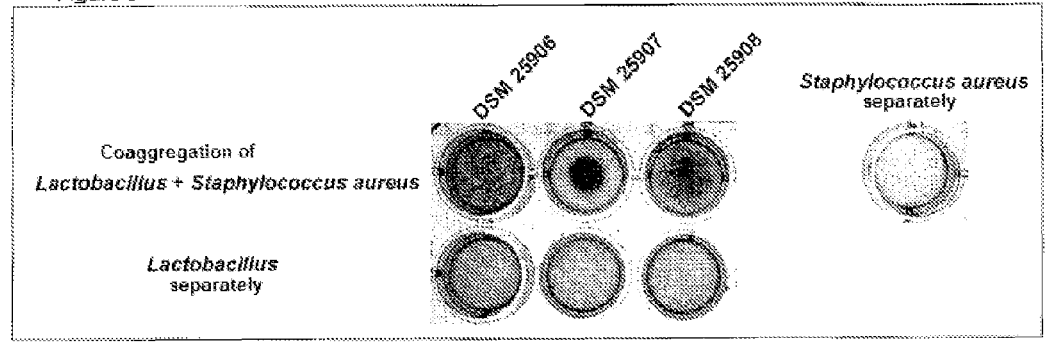

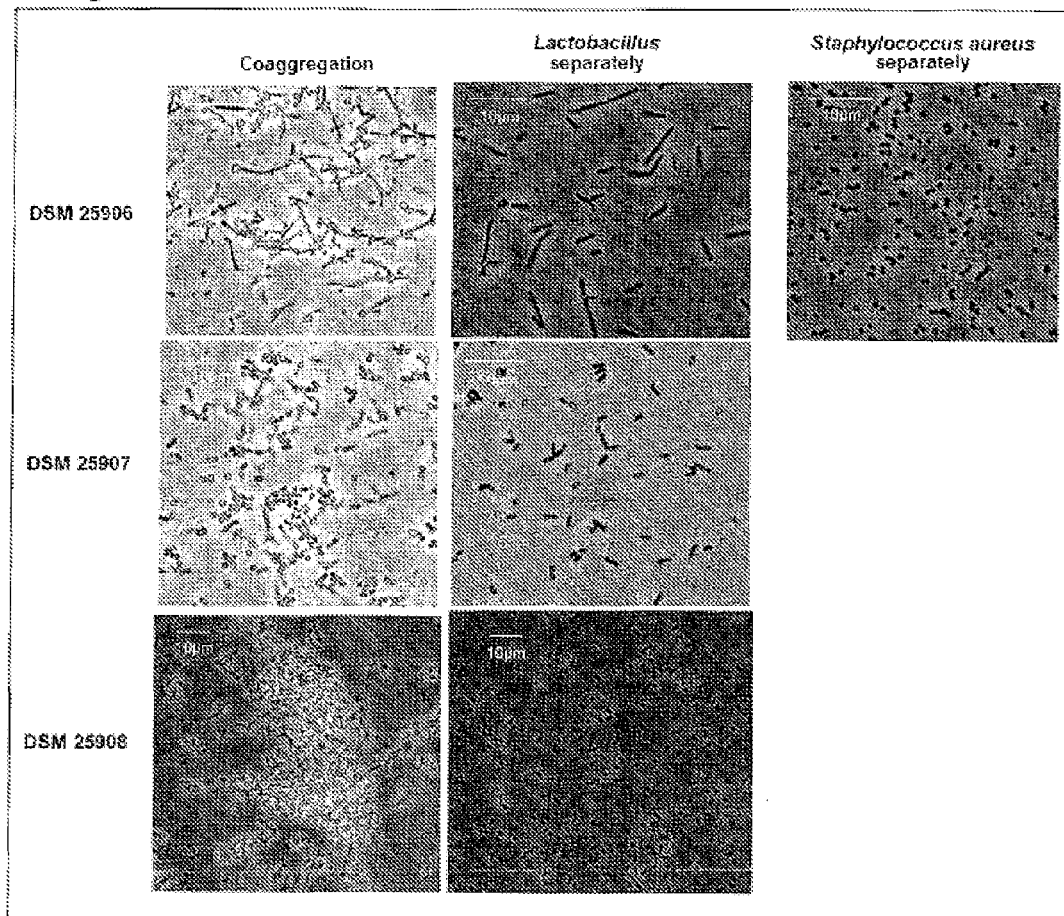

LACTIC ACID BACTERIA THAT CO-AGGREGATE WITH PATHOGENIC BACTERIA

CROSS-REFERENCE TO RELATED APPLICATIONS

This is the U.S. national stage of International application PCT/DE2012/100129, filed May 7, 2012 designating the United States, which claims priority to German application DE 10 2011 101 134.3, filed May 6, 2011.

The present invention relates to novel lactic acid bacteria, analogs or fragments thereof as well as compositions containing same, in particular for use as probiotics and/or in physical hygiene and therapy. The present invention relates in particular to the use of the novel lactic acid bacteria and/or compositions containing same for treatment and/or prevention of all diseases that may be caused by *Staphylococcus aureus* or *Pseudomonas aeruginosa*.

In addition, the development described here presents an innovative biological product in the form of GRAS microorganisms, lactic acid bacteria which can be used as an antimicrobial additive having a specific action for prevention and topical treatment of skin infections and for accelerating the treatment of chronic wounds.

Furthermore, the present invention relates to the use of the microorganism according to the invention, or an analog or fragment thereof in compositions or pharmaceutical products or cosmetic products or medical products as well as for skin or surface disinfectants.

BACKGROUND

The main function of the skin is to protect the underlying tissue from the external environment. It thus prevents among other things the penetration of pathogenic microorganisms into the body. The skin and mucous membranes are of course populated by a wide variety of microorganisms which often live as commensals in a relatively stable composition on the surface and support the protective function of the skin. In the ideal case bacteria having a positive health effect will be dominant over harmful microorganisms occurring at the same time. If this system gets out of balance, negative effects on the person's health and well-being are virtually predestined.

Pathogenic microorganisms have the ability to adhere specifically to the structures of the epidermis through binding proteins. For example, the presence of adhesins with which the microorganism can adhere to fibronectin structures is known to occur with the pathogenic strain *Staphylococcus aureus* (Bingham, R. J. et al. 2008, O'Neill, E. et al., 2008).

Pathogenic microorganisms usually have a higher potential for adhering to the host, which thus explains the increased virulence. The presence of extremely small lesions or other injuries in the top layers of skin increases the risk of invasion of pathogenic microorganisms.

Furthermore, bacterial infections of the wound surfaces especially in healing of wounds may lead to complications. There is the risk first that acute wound will not heal and will lead to chronic wounds. The microflora of these chronic wounds is highly complex and it is known that a variety of microorganisms can have a deleterious effect on the wound healing process (Davies et al. 2004, Kirketerp-Moller et al. 2008).

Aerobic bacteria, e.g., *Pseudomonas aeruginosa* and *Staphylococcus aureus* have be identified as the main pathogens in wounds. The inflammatory phase of wound healing normally serves to combat potentially pathogenic microorganisms and for cell regeneration. However, poorly healing or refractory wounds often occur in patients who are already immunosuppressed and have a reduced inflammatory response. This weakened immune response can no longer provide effective defense against primary wound bacteria, so the bacteria penetrate into the wound and form colonies, which are organized as biofilms (James et al. 2008).

The biofilms are not only resistance to the defense system of the host but also planktonic cells or microcolonies (Fux et al. 2005, Sheldon 2005). Due to the impaired immune system, the biofilm keeps the wound healing process in the inflammation phase with the result that there are elevated concentration of matrix metalloproteins such as elastase, plasmin and thrombin, for example, which in turn degrade the growth factors and their receptors that are essential for healing (Mast and Schultz 1996).

Furthermore, the elevated concentrations of free oxygen radicals and inflammatory cytokines led to severe damage to the host cells (James et al. 2003, Moseley et al. 2004).

Therapeutic agents capable of eliminating the biofilm and thus combatting the causes of chronic and refractory wounds have been described in the prior art.

STATE OF THE ART

Wound infections are also treated according to the current state of the art by complex antibiotic therapies which do not always lad to a cure because the aforementioned wound organisms do not response to such a treatment because of their adaptability and resistance mechanisms including their ability to form a biofilm. Skin care products such as pH-optimized shower gels, washing lotions, shower oils and body lotions are available for prophylactically preventing skin damage especially in immunosuppressed patients, e.g., those with atopic dermatitis, eczema, seborrheic dermatitis.

The main pathogen *S. aureus* is a disease pathogen which can survive without nutrients for up to 7 months. It survives on laundry and door handles, light switches, floor covering and on the side of the bed (Julia Bidder 2010). It does not cause symptoms in healthy people but if one's immune system is weakened as in the case of a wound infection, the microorganism will proliferate and cause inflammations that do not heal well, skin ulcers, furuncles, lung infections, urinary tract infections and life-threatening blood toxicity, eye infections, middle ear infections. The infections may jump over to practically any organ. Certain factors may promote an infection with *Staphylococcus aureus*, for example, a weakened immune system, diabetes mellitus, pre-existing skin damage (desquamation or neurodermatitis), skin injuries (e.g., due to accidents, surgery, catheters), the elderly with decubital ulcers and bedridden patients, obese patients whose own skin offers a moist reservoir for the development of microbial infections.

The antibiotic methicillin is no longer effective against methicillin-resistant strains of *S. aureus* (MRSA). What this means in practice is that this these strains are multiresistant against three or more antibiotics. Only so-called reserve antibiotics are of help now against these strains. German clinics estimate the increased cost for treatment of a MRSA patient at 1600 to 4300 Euro per day (Julia Bidder 2010).

*Pseudomonas aeruginosa* is another main pathogen, which is also frequently encountered in nosocomial infections and has multiple antibiotic resistances due to its metabolism and its cell membrane structure. *P. aeruginosa* accounts for almost 10% of all hospital infections and is one of the most common nosocomial microorganisms in Germany. The spectrum of disease caused by these bacteria is extensive. Hemolysis ability is one of the first triggering factors for this, as are pathogenicity factors such as exotoxin A (ADP ribosyl transferase) and the cytotoxins exoenzyme S and exoenzyme U, which produce the bacterium. The most common manifestation is pneumonia with cystic fibrosis, which can be especially serious in immunosuppressed patients and AIDS patients. Urinary tract infections, enterocolitis, meningitis, otitis externa ("swimmer's ear"), infections of burns or keratitis in users of contact lenses may also be triggered.

Lactic acid bacteria are generally used as probiotic bacteria to protect against the gastrointestinal disease caused by disease pathogens because they often produce antibacterial substances in addition to lactic acid. These lactic acid bacteria (Lactobacillales, lactobacilli or lactic acid bacteria) form an order of gram-positive bacteria that are always anaerobic or mostly aerotolerant and are characterized in that they degrade sugar to lactic acid (lactic acid fermentation). The order of Lactobacillales includes the families Lactobacillaceae, Aerococcaceae, Carnobacteriaceae, Enterococcaceae, Leuconostocaceae and Streptococcaceae. The *Bifidobacterium bifidum* species was formerly classified with the lactobacilli (*Lactobacillus bifidum*), but according to the information available today, it is which is not closely related to this order phylogenetically. However, it is still treated as a lactic acid bacterium with regard to the metabolism. Lactic acid bacteria are also very important in the food industry, where they are used to produce milk products but may also occur as pests (e.g., in a beer brewery. Lactic acid bacteria are classified as apathogenic.

The use of probiotic bacterial for dishwashing agents is also known in the prior art (e.g., WO 2010/130563), so the negative effects of dishwashing on skin can be reduced. It also has a skin care effect.

The use of microorganisms in cosmetic skin treatment agents is already known. Thus, U.S. Pat. No. 6,790,434, for example, describes the use of such microorganisms in cosmetic skin treatment agents in combination with a plant extract from the extracellular matrix to counteract the UV-induced skin damage. However, this source does not disclose the use of these microorganisms in detergents and cleaning agents.

In addition, the use of certain *Bacillus* species in sanitary cleaning agents is known. Thus WO 97/25865 describes the use of *Bacillus* species in sanitary cleaning agents because they prevent the pathogens from reproducing and are capable of degrading organic soiling. However, this does not describe the use of microorganisms having a beneficial effect on the skin.

In the meantime, the oral dosage form of probiotic bacteria was disclosed in WO 2005/117921, where the dosage form contains at least one genus of probiotic microorganisms, where the dosage form and/or the bacteria is/are provided with a coating that contains cellulose ether.

The object of the present invention is to provide an agent or composition for acute and prophylactic treatment of wound infections and skin diseases and/or skin irritation without having the disadvantages or shortcomings of the prior art.

DESCRIPTION OF THE INVENTION

This object is achieved by the independent claims. Preferred embodiments are derived from the dependent claims.

The present invention relates to a microorganism belonging to the order of lactic acid bacteria or an analog, fragment, derivative, mutant or combination thereof, wherein the microorganism or analog, fragment, derivative, mutant or combination therefore can coaggregate with at least one pathogenic microorganism wherein the pathogenic microorganism is selected from the group comprising *Staphylococcus aureus* or *Pseudomonas aeruginosa*. It was completely surprising that lactic acid bacteria which aggregate with infectious bacterial strains in particular can be provided, in particular by coaggregating with them and thus reducing the local concentration of the microorganisms, inhibiting their growth or even killing them or preventing the formation of a biofilm. This constitutes a departure from the prior art with some important advantages in comparison with traditional treatment options of the prior art because no antibiotic treatment is necessary but instead the pathogenic lactic acid bacteria can be used. Furthermore, the production of specific lactic acid bacteria constitutes an inexpensive alternative in comparison with production of antibiotics and the following cost of treatment. Treatment with lactic acid bacteria which are derived specifically against these microorganisms and do not cause any further resistance of the microorganisms is a unique approach in the battle against pathogenic microorganisms.

In the sense of the present invention, coaggregation describes a particular adhesion or binding of genetically different bacterial species to one another whereas coadhesion refers in particular to the adhesion or binding of genetically identical bacterial species. Therefore in this regard it was even more surprising that lactic acid bacteria can bind to the pathogenic bacteria, thereby resulting in coaggregation through specific binding in particular.

The invention relates in particular to a microorganism or an analog, fragment, derivative, mutant or combination thereof wherein the ability to coaggregate the at least one pathogenic microorganism exists even after a biological, chemical or physical treatment. With the preferred microorganism or analog, fragment, derivative, mutant or combination thereof, the capability for coaggregation of the at least one pathogenic microorganism preferably exists even at a pH of between approx. 3 and approx. 8. In a preferred embodiment the microorganism or the analog, fragment, derivative, mutant or combination thereof in particular has the capability for inhibiting the formation of a biofilm of the at least one pathogenic microorganism.

It is preferable in particular that the microorganism or the analog, fragment, derivative, mutant or combination thereof is selected from the group comprising *Lactobacillus lactis, Lactobacillus helveticus, Lactobacillus jensenii, Lactobacillus acidophilus, Lactobacillus bulgaricus, Lactobacillus amylovorus, Lactobacillus delbrueckii, Lactobacillus casei, Lactobacillus crispatus, Lactobacillus gasseri, Lactobacillus johnsonii, Lactobacillus paracasei, Lactobacillus pentosus, Lactobacillus rhamnosus, Lactobacillus curvatus, Lactobacillus plantarum, Lactobacillus brevis, Lactobacillus buchneri, Lactobacillus fructivorans, Lactobacillus hilgardii, Lactobacillus fermentum, Lactobacillus reuteri, Lactobacillus viridescens, Bifidobacterium bifidum* or analogs, derivatives, fragments or mutants thereof.

Microorganisms or analogs, fragments, derivatives, mutants or combinations thereof according to the present disclosure may be used, wherein the microorganism is selected from the group consisting of the following microorganisms that have been deposited in accordance with the Budapest Treaty with the German Collection for Microorganisms and Cell Cultures ("DSM" located Inhoffstrasse 7B, 38124 Braunschweig, Germany), an international deposit authority, and their deposit numbers are: DSM 25906, DSM 25907, DSM 25908, DSMZ 25909, DSM 25910, DSM 25911, DSM 25912, DSM 25913, DSM 25914 and DSMZ 25915. The respective deposits were all made on Apr. 18, 2012.

In another aspect the invention relates to a composition comprising at least one microorganism or analog, fragment, derivative, mutant or combination thereof. The term composition in the sense of the present invention may be used as synonymous with the term formulation. The preferred composition may also contain a vehicle or excipient selected from the group comprising cosmetically acceptable vehicles or excipients, pharmaceutically acceptable vehicles or excipients or dermatologically acceptable vehicles or excipients.

The composition may preferably be in the form of a powder, stick, aerosol spray, pump spray, cream, dispersion, emulsion, foam, ointment, spray, aerosol, powder, stick, cloths, lotion, suspension, solution, gel or on a substrate. It is preferable in particular for a composition to be in the form of a skin cream, skin washing lotion or a skin ointment.

In a preferred embodiment the composition may be present in solid, liquid, viscous form or as an aerosol. Furthermore, the preferred skin cream, skin washing lotion or skin ointment may be present in particular in solid, liquid or viscous form or as an aerosol.

The preferred composition may also preferably comprise probiotics, antiseptics or other antibacterial substances, whereby in a preferred composition it is a pharmaceutical, veterinary, cosmetic or food composition.

In another preferred embodiment, the composition preferably also comprises builder substance, surface-active surfactants, enzymes, organic and/or inorganic peroxygen compounds, peroxygen activators, water-miscible organic solvents, sequestering agents, electrolytes, pH regulators, thickeners, soil release agents, optical brighteners, graying inhibitors, dye transfer inhibitors, foam regulators, and/or other coloring agents.

In addition, it may be preferable for the composition to comprise at least one substance selected from the groups
 a. Active ingredient which have a positive influence on the condition of the skin, in particular active ingredients for having a positive influence on elderly skin, in particular in combination with bioquinones, in particular ubiquinones Q10, creatine, creatinine, carnitine, biotin, isoflavone, cardiolipin, lipoic acid, antifreezing proteins, arctiin, hops and hop-malt extracts,
 b. Promoting agents for restructuring the connective tissue, in particular isoflavonoids,
 c. Active ingredients for supporting skin functions on dry skin in particular, vitamin C, biotin, carnitine, creatine, propionic acid, green tea extract, eucalyptus oil, urea and mineral salts, in particular NaCl, marine minerals and osmolytes,
 d. Active ingredients for relieving and/or having a positive influence on irritated skin conditions, in particular sericosides, various extracts of the licorice, licochalcones, in particular licochalcone A, silymarin, silyphos and/or dexpanthenol.

It is preferable for the microorganism to be present in the composition in inactivated, viable or nonviable form. In addition, the microorganism may be present in the composition preferably in encapsulated, spray-dried and/or lyophilized form. It is also preferable for the microorganism to be present in particular in the form of a cell lysate in the composition. In a preferred embodiment the microorganism is present in the composition in particular in an amount with an amount by weight of 0.001% by weight to 10% by weight, preferably 0.005% by weight to 5% by weight, especially preferably 0.01% by weight to 3% by weight.

The invention also relates to a method for identifying and/or selecting a lactic acid bacterium having the property of coaggregating with a pathogenic microorganism selected from the group comprising *Staphylococcus aureus* or *Pseudomonas aeruginosa*, where the method includes at least the following steps:
 a. Incubating the pathogenic microorganism to form a biofilm,
 b. Adding a lactic acid bacterium to be investigated and incubating to form a mixture to form the coaggregation between the pathogenic microorganism and the lactic acid bacterium to be investigated,
 c. Separating the unbound lactic acid bacteria by removing the supernatant and
 d. Determining the biofilm from the standpoint of coaggregated lactic acid bacteria.

This method may preferably also comprise the following additional step:
 Investigating the inhibition of biofilm by the pathogenic microorganisms, whereby the lactic acid bacteria to be investigated are added during the incubation of the biofilm-forming pathogenic microorganism.

Furthermore, this method may be supplemented by the following method step in a preferred embodiment:
 Quantification of the biofilm formation by removal of the unbound cells by means of a measurement of the optical density in comparison with a control without addition of the lactic acid bacteria to be tested.

In another aspect, the invention relates to the use of the composition preferably from producing a pharmaceutical drug, a medical product or a cosmetic for treatment or prevention of skin diseases, in particular staphylococcal-scalded skin syndrome, impetigo contagiosa, folliculitis superficialis, impetiginization, skin abscesses, furuncles, carbuncles, abscesses, phlegmons, dry skin, itching skin, reddened skin, irritated skin, extremely oil skin, acne, diabetic foot, decubital ulcer, neurodermatitis, acute lymphadenitis, pilonidal cysts, pilonidal fistulas, pilonidal sinus, pilonidal fistula, pilonidal cysts, local infections of the skin and the subcutaneous tissue, pyoderma, purulent dermatitis, septic dermatitis, suppurative dermatitis, dermatitis and eczema, atopic eczema, seborrheic eczema, diaper rash, allergic contact dermatitis, seborrheic dermatitis, exfoliative dermatitis, toxic contact dermatitis, chronic lichen simplex, prurigo, pruritus and other forms of dermatitis, papulosquamous skin diseases, psoriasis, parapsoriasis, diseases of the integumentary appendages, scarring of alopecia, folliculitis decalvans as well as other diseases of the skin and subcutaneous tissue, crural ulcers, skin injuries, scraps and scabs, wounds after accidents or surgeries.

In a preferred embodiment the composition may be used to produce a cleaning agent or disinfectant for treatment of surface. In addition, the composition may advantageously also be used to produce a product which is used in the area of physical hygiene, medical products and prophylaxis.

The composition is preferably used to produce a lotion, a shake mixture, a powder, a hydrogel, a cream, cresa, ointment, fatty ointment or paste for application to a skin surface.

It has advantageously been found that the composition can preferably be used to produce an antimicrobial additive having a specific action for local treatment of skin infections and for accelerating the healing of chronic wounds. The composition may preferably be used prophylactically or curatively. Furthermore, the composition may preferably be applied topically.

In another aspect, the invention relates to a kit for a hygiene treatment comprising microorganisms or the composition and physical hygiene devices or equipment, rinses and/or pastes.

In a preferred application form, the invention may be used as an antimicrobial additive for a spray or washing solution for animals, in particular for dogs, horses, cats and rodents (rabbits, hares, hamsters, guinea pigs) and commercial animals such as chickens, pigs and cattle to significantly reduce the microbial burden on the skin, fur and feathers.

The present invention thus also relates to microorganisms, in particular lactic acid bacteria, analogs, mutants, derivatives or fragments thereof as well as compositions containing these, in particular for use for treatment or prevention of infants [sic again], toddlers, children, healthy people, elderly, immunosuppressed people, people with pathological skin changes (in particular staphylococcal scalded skin syndrome, impetigo contagiosa, folliculitis superficialis, impetiginization, skin abscesses, furuncles (furunculosis), carbuncles (abscesses), phlegmons, dry skin, itchy skin, reddened skin, irritated skin, extremely oily skin, acne, diabetic foot, decubital ulcers, neurodermatitis, acute lymphadenitis, pilonidal cyst (including pilonidal fistulas, pilonidal sinus, coccygeal fistula, coccygeal cysts), other local infections of the skin and the subcutaneous tissue (e.g., pyoderma, purulent dermatitis, septic dermatitis, suppurative dermatitis); also various forms of dermatitis and eczema (e.g., atopic eczema, seborrheic eczema, diaper rash, allergic contact dermatitis, seborrheic dermatitis, exfoliative dermatitis, toxic contact dermatitis, chronic lichen simplex, prurigo, pruritus and other forms of dermatitis); they can also be used to treat papulosquamous skin diseases (psoriasis, parapsoriasis), diseases of the integumentary appendages (e.g., alopecia with scarring including folliculitis decalvans), plus other diseases of the skin and subcutaneous tissue (e.g., crural ulcers), people with pre-existing damage to the skin (e.g., dry skin), skin injuries (e.g., scabs, wounds, including those after accidents or surgery) or in commercial animals and household pets.

The preferred microorganisms are namely the microorganisms that belong to the order of lactic acid bacteria or analogs, derivatives, mutants or fragments thereof have the capability for coaggregation in particular, preferably specific binding of at least one pathogenic microorganism which is selected from the group of *Staphylococcus aureus* and/or *Pseudomonas aeruginosa*. It was completely surprising that the preferred lactic acid do not cause any coaggregation or binding of the commensal skin bacteria or microorganisms such as *Corynebacterium jeikeium*, *Micrococcus luteus*, *Propionibacterium acnes* or in particular *Staphylococcus epidermidis*. For example, *Staphylococcus epidermidis* is a largely unremarkable commensal organism of the skin flora. In the interaction of the various microorganism found in or on the skin, the species is present in the healthy skin flora of many mammals and is in a microbial equilibrium with them—at least on healthy skin. Therefore, an influence on this bacterium, for example, due to aggregation and therefore an influence on other microorganisms used in a targeted manner in physical hygiene would not be preferred within the scope of the present invention.

In other words the preferred lactic acid bacteria coaggregates specifically with the pathogenic bacteria *Staphylococcus aureus* and/or *Pseudomonas aeruginosa*. Nothing of the type is derived from the prior art. The prior art describes only lactic acid bacteria which also exhibit a binding to commensal microorganisms so that they cannot be used without causing adverse effects. In contrast with those, the preferred lactic acid bacteria do not exhibit any binding or coaggregation of commensal skin bacteria or other pathogenic microorganisms that populate the skin flora. According to another preferred embodiment, the lactic acid bacteria according to the invention do not have the ability to bind to commensal microorganisms on the skin.

It is known to those skilled in the art that healthy skin is densely occupied with microorganisms such as bacteria and fungi in the form of commensals or mutual. These microorganisms are a natural component of the skin surface and are summarized by the term skin flora. The microorganisms subsumed under the term skin flora are an important prerequisite for protecting the skin itself and the body as whole from pathogenic organisms and are part of the biodome. In this regard it is especially advantageous that the preferred lactic acid bacteria do not bring the skin flora out of equilibrium but instead merely bind to the pathogenic bacteria *Staphylococcus aureus* and/or *Pseudomonas aeruginosa* and/or coaggregate with them.

The microorganisms have specific adhesive properties in particular and form coaggregates with the pathogenic microorganisms *Staphylococcus aureus* and/or *Pseudomonas aeruginosa*. However, it is also preferable for the lactic acid bacteria to also coaggregate specifically with other pathogenic species of the microorganisms *Staphylococcus* or *Pseudomonas* or to at least interact with them.

Not least of all the microorganisms according to the invention have properties to prevent the formation of a biofilm. Due to the fact that the preferred lactic acid bacteria coaggregate with the pathogenic bacteria and/or have adhesive properties with respect to them, the pathogenic microorganisms can be masked, which leads to concealment of many pathogenicity factors and thus to a reduction in the bacterial burden and/or to inhibition of the biofilm formation, e.g., by masking and/or binding the corresponding surface adhesins of the pathogenic bacteria.

Although the invention relates in particular to a group of lactic acid bacteria, there is still uniformity of the teaching according to the patent application. The claimed microorganisms have a common property or effect. The sum of the structural or functional commonalities leads to the functional relationship between the coaggregation of *Staphylococcus aureus* and/or *Pseudomonas aeruginosa*, the non-binding of commensal microorganisms of the skin and the prevention of formation of biofilm and/or the destruction of established biofilms by *Staphylococcus aureus* and/or *Pseudomonas aeruginosa*. These common features therefore do not constitute an arbitrary sum of features but instead from the common fingerprint of the claimed microorganisms so to speak which advantageously permits and characterizes the suitability of these microorganisms for this purpose.

The preferred microorganisms in particular lactic acid bacteria are selected from the group comprising *Lactobacillus lactis, Lactobacillus helveticus, Lactobacillus jensenii, Lactobacillus acidophilus, Lactobacillus bulgaricus, Lactobacillus amylovorus, Lactobacillus delbrueckii, Lactobacillus casei, Lactobacillus crispatus, Lactobacillus gasseri, Lactobacillus johnsonii, Lactobacillus paracasei, Lactobacillus pentosus, Lactobacillus rhamnosus, Lactobacillus curvatus, Lactobacillus plantarum, Lactobacillus brevis, Lactobacillus buchneri, Lactobacillus fructivorans, Lactobacillus hilgardii, Lactobacillus fermentum, Lactobacillus reuteri, Lactobacillus viridescens, Bifidobacterium bifidum* or analogs, derivatives, fragments or mutants thereof; these microorganisms are associated through the functional relationship with one another to form a uniform idea of the invention, such that they share the properties and/or effects, namely that they specifically coaggregate with the pathogenic bacteria *Staphylococcus aureus* and/or *Pseudomonas aeruginosa*, do not bind any commensal microorganisms of the skin and/or mucous membranes and also prevent the formation of biofilm by *Staphylococcus aureus* and/or *Pseudomonas aeruginosa*. These lactic acid bacteria include in particular microorganisms or analogs, fragments, derivatives, mutants or combinations thereof selected from the group comprising the following microorganisms deposited with the German Collection for Microorganisms and Cell Cultures under the code numbers DSM 25906, DSM 25907, DSM 25908, DMZ 25909, DSM 25910, DSM 25911, DSM 25912, DSM 25913, DSM 25914 and DSMZ 25915. It was completely surprising that a group of lactic acid bacteria could be identified that had identical advantageous properties. No bacteria, in particular no lactic acid bacteria that combine all these properties while also being apathogenic and not causing any damage to or influence on the natural flora of the skin have been described. It has also been found that application of the preferred lactic acid bacteria, whether as a composition or otherwise, prevents the binding and invasion of host cells by *Staphylococcus aureus* and/or *Pseudomonas aeruginosa*. The cause of this is so far unknown but should be identified by additional experiments.

Another surprising advantage of the preferred microorganisms, in particular lactic acid bacteria is that they can also be used prophylactically. Another surprising advantage of the preferred microorganisms in particular lactic acid bacteria is that they can also be used prophylactically. In other words the lactic acid bacteria and/or a composition containing them may be applied prophylactically to an area of skin at risk and/or to groups of people or animals at risk without resulting in any damage to the skin or skin flora. It is known, for example, that open wounds can develop at pressure points in people who must be bedridden for a length period of time. Initial experiments have shown that a prophylactic treatment of these regions can prevent the development of open wounds or can at least protect against additional infections caused by *Staphylococcus aureus* and/or *Pseudomonas aeruginosa*.

In a sense of the present invention the skin in preferred embodiments is understood in particular to be the external organ of the human or animal body which serves to delineate the inside from the outside. A skin area in the sense of the present invention includes in preferred embodiments components of the top layer of skin, the corium or true skin or the subcutaneous tissue. The top layer of skin (epidermis) also consists of the following layers according to the invention: horny layer (stratum corneum), lucid layer (stratum lucidum), granular layer (stratum granulosum), spiny cell layer (stratum spinosum) and/or basal layer (stratum basale). Each modification of cells in this area constitutes a cell modification in an area of skin in the sense of the present invention.

The dermis or corium which may also be a component of the area of skin according to the invention preferably consists of connective tissue fibers and serves to provide nourishment and anchoring for the epidermis. The capillarized blood vessel system in the borderline zone with the epidermis also belongs to a skin area in the sense of the invention as do the sebaceous glands and sudoriferous glands or sweat glands. The dermis in the sense of the present invention may be subdivided into a stratum papillare and a stratum reticulare. In addition, an area of skin in the sense of the invention may be any area, i.e., any location in or on the subcutaneous tissue (subcutis) or tissue in the interior of the body or any organ or organ component. A tissue barrier delineating an organ from the surrounding structures may be a skin in the sense of the present invention. In addition, the inventive concept of an area of skin may also be understood to include integumentary appendages such as hair, sebaceous glands, arrectores pilorum muscles, nails, horns and sudoriferous glands, in particular the eccrine and apocrine sudoriferous glands but also the mammary glands. Any cell modification in particular a cell growth that deviates from the normal can be treated with the agents according to the invention, preferably without being limited to the external areas of skin. However, the areas of skin in the sense of the present invention may also include the inguinal skin such as that on the fingers or the soles of the feet or the integument and the skin appendages associated therewith.

The tolerability of the lactic acid bacteria of the skin is a prerequisite for successful treatment of skin infections and bacterial infections in wounds or other diseases or symptoms in which microorganisms from the staphylococcal or pseudomonal groups occur.

The preferred composition may be contained in particular in a soap, a lotion, a powder, a syndet, a foam, a stick, an emulsion, a spray, a cream, a gel, a shampoo, a liquid soap or a deodorant. It is also preferable for the composition to be used in particular as a probiotic which may be added as a detergent, rinse agent, cleaning agent or disinfectant (e.g., soaps, powders, pastes, solutions, emulsions, lotions), cleaning and/or disinfection towels, shampoos, rinses or applications for the skin, hair and/or scalp, creams, ointments, skin cleaning lotions and/or skin care lotions, solutions (e.g., as drops, sprays, rinse) for use in or on the eyes, ears, mouth, nose or throat and/or may be incorporated into bandages or wound dressings to suppress the formation of pathogenic microorganisms, to bind them, to remove them as an aggregate and/or to inhibit them or to kill them and thereby to reduce their numbers.

It was completely surprising that the advantages of the composition according to the invention could be improved yet again by incorporating it into the aforementioned pharmaceutical forms. Those skilled in the art are familiar with other formulation concepts for introducing the composition according to the invention into vehicle substances, for example, such as emulsions or other products for dermal application, e.g., liquid forms which may preferably be anhydrous or hydrous, where the aqueous forms can be divided according to the invention into monophase systems and multiphase systems. In addition, semisolid forms which are anhydrous or hydrous may be used, where again it is possible to divide them into single phase systems and multiphase systems in which semisolid forms containing water are also possible. Solid forms which are lipophilic or hydrophilic may preferably also be used. Examples of such forms include, for example, fat-based ointments, foams, powders, sticks, gel creams, hydrodispersion gels, watery emulsions, lotions, ointments, sprays and creams in addition to those forms already mentioned above. Those skilled in the art are aware here that such vehicle substances can first be differentiated into those that are rich/valuable and those that are fresh and light based on the feeling on the skin and secondly can be differentiated into those with a low viscosity and others with a high viscosity in terms of the viscosity whereas hydrogels or hydrocreams and/or O/W emulsions or W/O emulsions have a high viscosity. When liquid application forms are used, they can be subdivided—as explained above—into hydrous and anhydrous systems. Of the anhydrous systems, apolar systems, polar systems without emulsifiers and polar systems with emulsifiers are especially preferred. Of the hydrous systems, single phase systems such as solutions and microemulsions are preferred; of the multiphase systems, multiple emulsions W/O emulsions or O/W emulsions are preferred. Of the solid/liquid systems, preferred forms include suspensions or liquid/solid/liquid systems such as suspension systems/emulsion systems. Those skilled in the art are aware of various possibilities for supplying such vehicles. With the O/W emulsions, preferred pharmaceutical leading substances include O/W emulsifiers, W/O emulsifiers, liquid hydrophilic ingredients and liquid lipophilic ingredients. With the W/O emulsions, preferred pharmaceutical leading substances include W/O emulsifiers, O/W emulsifiers, liquid and semisolid lipophilic ingredients, gel-forming agents, liquid hydrophilic ingredients and/or salts.

Of the semisolid preferred vehicle substances, anhydrous systems as well as hydrous systems are preferred for various applications. Anhydrous systems may consist of apolar system or polar systems without emulsifiers such as lipogels, oleogels or polyethylene glycol gels and/or may consist of apolar systems with emulsifiers on O/W absorption bases or W/O absorption bases. The hydrous systems may preferably consist of single phase systems such as hydrogels or microemulsion gels or multiphase systems such as O/W creams, W/O creams or amphiphilic systems. The preferred semisolid preparations are spreadable preparations for application to the skin in the temperature range between room temperature and skin temperature or for application to the mucous membranes, where they have a topical effect, where they transport the active ingredients or have a softening or protective effect on the skin. Preferred preparations include ointments in the narrower sense, creams, gels and/or pastes. In addition to the ointments, creams, gels and pastes, oleogels may also be used as semisolid transparent single phase systems. Those skilled in the art are aware of various anhydrous compounds for formulating semisolid systems from U.S. Pat. No. 6,187,323 or Aiache et al. 2001, including, for example, the compound of an olegogel and a hydrogel, which may be referred to as a bigel according to the present invention. In addition, hydrodispersion gels or various lipids may be used to provide vehicle substances according to the invention. When using lipids, organosilicon compounds and organocarbon compounds may be used to supply lipid phases in disperse systems, where the organocarbon compounds may be supplied with the help of non-hydrolyzable lipids or hydrolyzable lipids (glycerols) or wax esters, for example. The advantages of such systems include an improved suppleness of the skin and an increase in elasticity as well as the ability to have the effect of increasing release of the substances and penetration thereof, depending on the lipid composition. Those skilled in the art will know which lipids they must use to increase or decrease the penetration within a time parameter, for example.

Additional preferred vehicle substances include, for example, hydrodispersion gels and/or microcapsules, microspherules or pellets (macrobeads). The vehicles mentioned serve to increase stability and ensure a minimum application period on the skin. The preferred semisolid single phase systems can be prepared with the help of the following pharmaceutical leading substances: liquid hydrophilic ingredients in particular water and (poly)alcohols, hydrophilic gel-forming substances, salt-forming substances and W/O emulsifiers, O/W emulsifiers, liquid, semisolid and solid lipophilic ingredients as well as lipophilic gel-forming substances and builders. Those skilled in the art will know how they must combine these substances to achieve a certain effect.

Those skilled in the art will also know of other pharmaceutical preparations for dermal products. According to the present patent application, for example, all the pharmaceutical compounds disclosed in the citation by Daniels and Knie in *JDDG;* 2007, 5:367-383. Those skilled in the art are aware that different pharmaceutical preparations have different effects in the skin and they will apply galenic composition to the skin in different amounts. The contents of *JDDG;* 2007, 5:367-383 are herewith incorporated into the disclosure content of the teaching according to the patent application. Preferred products according to the invention include, for example, lipophilic or hydrophilic solutions, lipophilic or hydrophilic emulsions, lipophilic or hydrophilic suspensions, special liquid preparations, hydrophobic or hydrophilic ointments, water-emulsifying ointments, lipophilic, hydrophilic or amphiphilic creams, hydrogels, hydrophobic or hydrophilic pastes and/or powders.

Experiments have shown that the preferred lactic acid bacteria in particular lactobacillus cells form coaggregates in contact with *Staphylococcus aureus* and/or *Pseudomonas aeruginosa* cells. Due to the formation of coaggregates, *Staphylococcus aureus* and/or *Pseudomonas aeruginosa* is prevented from penetrating into skin wounds in particular or settling on the skin and forming colonies, and establishing, adhering and forming biofilms. The *Staphylococcus aureus* and/or *Pseudomonas aeruginosa* cells in particular their cell surface are masked by the lactic acid bacteria in particular *lactobacillus* cells, so that the *Staphylococcus aureus* and/or *Pseudomonas aeruginosa* cells are preferably no longer capable of binding to skin epithelial cells. Since *Staphylococcus aureus* and/or *Pseudomonas aeruginosa* are prevented from binding to the skin epithelial cells, inflammation reactions fail to occur and/or skin irritation is reduced or prevented. The *Staphylococcus aureus* and/or *Pseudomonas aeruginosa* cells in particular their cell surface are bound by the lactic acid bacteria in particular *lactobacillus* cells. Then cell coaggregates consisting of *lactobacillus* cells and/or *Staphylococcus aureus* and/or *Pseudomonas aeruginosa* cells which can be removed (washed off) more easily and more efficiently and effectively from the skin, wounds and surfaces in general (fur, feathers, steel, plastic and metal surfaces) are formed in comparison with *Staphylococcus aureus* and/or *Pseudomonas aeruginosa* cells present individually or in small aggregates.

In the sense of the present invention, probiotic microorganisms comprise cells which have advantageous effects on human and/or animal bodies. A preferred composition is used as a probiotic composition and contains lactic acid bacteria, which have an advantageous effect on the human or animal body. Advantageous effects may consist in particular in improving the skin flora. In particular unwanted microorganisms such as *Staphylococcus aureus* and/or *Pseudomonas aeruginosa* in the skin flora can be inhibited by direct interactions with the probiotic microorganisms and the unwanted microorganisms and in particular by indirect interactions based on inhibition of the metabolism of the unwanted microorganism due to the expression products of the probiotic microorganism. Experiments have shown that the pathogenic microorganism *Staphylococcus aureus* and/or *Pseudomonas aeruginosa* do not exhibit any growth, i.e., no further reproduction of the cell mass after coaggregation by the preferred lactic acid bacteria and instead the cells are masked, bound in coaggregates and/or killed.

The analogs, mutants, derivatives or fragments of the lactic acid bacteria described here which are produced in particular by biological, chemical or physical treatment of the lactic acid bacteria and surprisingly exhibit the advantageous properties even after the treatment. The lactic bacteria are advantageously selected from the group comprising *Lactobacillus lactis, Lactobacillus helveticus, Lactobacillus jensenii, Lactobacillus acidophilus, Lactobacillus bulgaricus, Lactobacillus amylovorus, Lactobacillus delbrueckii, Lactobacillus casei, Lactobacillus crispatus, Lactobacillus gasseri, Lactobacillus johnsonii, Lactobacillus paracasei, Lactobacillus pentosus, Lactobacillus rhamnosus, Lactobacillus curvatus, Lactobacillus plantarum, Lactobacillus brevis, Lactobacillus buchneri, Lactobacillus fructivorans, Lactobacillus hilgardii, Lactobacillus fermentum, Lactobacillus reuteri, Lactobacillus viridescens, Bifidobacterium bifidum* and preferably selected from the group comprising the following microorganisms deposited with the German Collection for Microorganisms and Cell Cultures where they are numbered as DSM 25906, DSM 25907, DSM 25908, DSMZ 25909, DSM 25910, DSM 25911, DSM 25912, DSM 25913, DSM 25914 and DSMZ 25915.

Furthermore, it was surprising that the lactic acid bacteria, fragments, derivatives, mutants, analogs or combinations thereof would still have the advantageous properties even after physical, chemical and/or biological killing. For example, the preferred strains, namely DSM 25906, DSM 25907, DSM 2598, DSMZ 25909, DSM 25910, DSM 25911, DSM 25912, DSM 25913, DSM 25914 and DSMZ 25915, produce coaggregation of the pathogens, prevent formation of a biofilm and also do not exhibit any binding of commensal microorganisms, even after a heat treatment at 70° C. for 20 minutes or a treatment with ultrasound. Thus, the lactic acid bacteria, fragments, derivatives, mutants, analogs or combinations thereof may advantageously also be present in killed form in a preferred embodiment of the composition. The stability and usability of the composition can be substantially prolonged in this way. Furthermore, the composition may also be used in other areas of application, which do not allow the use of viable microorganisms. It was completely surprising that the lactic acid bacteria in the composition may be inactivated, viable or nonviable and nevertheless still be capable of specific binding and/or coaggregation with the pathogenic microorganisms. The composition may advantageously be used as a food, food additive or pharmaceutical agent, medical product, cosmetic, cleaning agent additive and as animal feed or beverage.

A preferred composition is one which contains the lactic acid bacteria according to the invention or analogs, fragments, mutants or derivatives thereof which have the ability to coaggregate at least one pathogenic microorganism selected from the group of *Staphylococcus aureus* and/or *Pseudomonas aeruginosa*, where the composition is used for physical hygiene, physical therapy and/or prevention.

The preferred microorganisms are representatives of the genus or order of lactic acid bacteria, i.e., gram-positive bacteria that produce lactic acid by fermentation of glucose. The microorganisms according to the invention are characterized on the one hand by the fact that they have the ability for specific coaggregation of at least one pathogenic microorganism which is selected from the group of *Staphylococcus aureus* and/or *Pseudomonas aeruginosa*. This binding leads to the formation of aggregates of the microorganisms according to the invention and the specifically bound pathogenic microorganisms. Due to the formation of coaggregates, the latter, i.e., the pathogenic microorganisms can easily be removed mechanically and in a targeted manner, for example, by rinsing off, which was impossible with the measures known in the past. Cell coaggregates consisting of *Lactobacillus* cells and/or *Staphylococcus aureus* and/or *Pseudomonas aeruginosa* cells can be removed (washed) off of the skin, wounds and surfaces in general more easily and more efficiently and more effectively (fur, feathers, steel, plastic and metal surfaces) in comparison with *Staphylococcus aureus* and/or *Pseudomonas aeruginosa* cells that are present individually or in small aggregates.

The term "specific binding" or "coaggregation" in the sense of the invention as well as in the fields of microbiology and hygiene in general, in particular human microbiology and physical hygiene, is understood to refer to the mutual recognition and adhesion of cells belonging genetically to different types of cells. On their cell surface, the bacteria here express receptors and structures for adhesins to other cell types that are used for adhesion between the cells. This adherence plays an excellent role in colonization with pathogenic microorganisms as well as with commensal microorganisms, so that an intervention in the adherence could result in far-ranging consequences. Due to the fact that the microorganisms according to the invention have the ability for specific binding, in particular, coaggregation with at least one microorganism from the group of *Staphylococcus aureus* and/or *Pseudomonas aeruginosa*, aggregates from the microorganisms according to the invention and the pathogenic microorganisms. The resulting coaggregates can be removed easily, for example, by rinsing surfaces, the skin, tissue and/or some other site or reservoir of colonization, so that the number of pathogenic microorganisms is definitely reduced. In addition, an initial and/or renewed adhesion to surfaces, the skin, tissues and/or other sites or reservoirs of colonization are prevented and/or reduced by masking the surface structures of the pathogenic microorganisms. If cells bind to one another and form aggregates, this process is referred to as aggregation in particular. If only one cell species is involved in this formation of an aggregate, that process is referred to as autoaggregation or self-aggregation. If at least two different cell species are involved in formation of the aggregate, this process is known in particular as coaggregation.

In the sense of the present invention "specific binding of at least one pathogenic microorganism" is understood in particular to refer to the property of the microorganisms according to the invention to bind at least one bacterium from the group of *Staphylococcus aureus* and/or *Pseudomonas aeruginosa*.

According to a preferred embodiment of the microorganisms according to the invention, they are also characterized in that the ability for specific binding to at least one pathogenic microorganism exists even after a biological, chemical or physical treatment, for example, a heat treatment at a minimum of 70° C. In other words, the preferred lactic acid bacteria may preferably be present in a preferred composition because the capability for a specific interaction or binding to pathogenic bacteria, in particular *Staphylococcus aureus* and/or *Pseudomonas aeruginosa*, is not affected and therefore binding or an interaction can be established.

Inactive or nonviable lactic acid bacteria cells may be especially advantageous because no metabolic activity can emanate from these lactic acid bacteria cells.

According to another preferred property of the lactic acid bacteria, the microorganisms according to the invention may also be characterized by thermal stability in addition to the property described above, namely the capacity for specific binding of at least one pathogenic microorganism selected from the Streptococcus pyogenes group, and they can survive a treatment at high temperatures, preferably at least approx. 60° C., more preferably at least 65° C. and even more preferably at least 70° C. for a period of at least 20 minutes, preferably 25 minutes and more preferably at least approx. 30 minutes and remain unchanged with respect to their capacity for coaggregation of said pathogenic microorganisms.

In a preferred embodiment of a composition, lactic acid bacteria that are inactivated, viable or killed or are parts and fragments thereof, e.g., enzymatic or mechanical cleavage products (e.g., French press, etc.) or metabolic products of these bacteria, inasmuch as they still have the capacity for coaggregation and/or preventing the formation of a biofilm. It is also preferable for the lactic acid bacteria to be used in encapsulated, spray-dried and/or lyophilized form, i.e., in encapsulated, spray-dried and/or lyophilized form in a preferred composition. Furthermore, it may be advantageous if the lactic acid bacteria are used in the form of digested cells.

Furthermore, it is preferable if the capability of the lactic acid bacteria according to the invention for specific binding to the pathogenic microorganisms persists even at a pH between approx. 3 and 8. This means that the lactic acid bacteria may be in a medium having a pH of 3 to 8 and still have their ability to bind Staphylococcus aureus and/or Pseudomonas aeruginosa. Those skilled in the art are aware of the fact that the skin has a slightly acidic pH. In this regard it is especially advantageous that the preferred lactic acid bacteria also exhibit their capability for coaggregation of Staphylococcus aureus and/or Pseudomonas aeruginosa in a broad pH range. The pH of the skin may vary, e.g., due to cosmetic products or in different regions of the body. The preferred lactic acid bacteria may advantageously in a wide pH range and/or have the preferred properties in the preferred range. The preferred lactic acid bacteria may thus advantageously be used universally in different areas of the body.

Furthermore, the invention described here is a composition, in particular an innovative probiotic, which also has coaggregation properties after a protease treatment (e.g., trypsin, trypsin TPCK-treated, lysozyme, proteinase K, pronase, thrombin, PNGase, pepsin, chymotrypsin, papain).

The lactic acid bacteria according to the invention surprisingly exhibit coaggregation properties in particular with Staphylococcus aureus and/or Pseudomonas aeruginosa in a broad temperature range of approx. 25° C.-42° C.

It will thus be clear to those skilled in the art that here as well as in all the statements of range given in the present invention characterized by such terms as "about" or "approximately" that the precise numerical range need not be indicated with the expression "about" or "approx./approximately" but instead even minor deviations up or down with regard to the number indicated are still within the scope of the present invention.

The binding of the lactic acid bacteria according to the invention to the pathogenic microorganisms listed preferably results in inhibition of the growth of these pathogenic microorganisms.

It was surprising that, due to the binding of the pathogenic microorganisms and the lactic acid bacteria according to the invention, an aggregate which is present as a sediment, is formed in particular after 5 to 100 minutes at room temperature without agitation.

Aerobic, mainly pathogenic bacteria in wounds are Staphylococcus aureus and/or Pseudomonas aeruginosa in particular. The inflammation phase of wound healing normally serves to combat potential pathogenic microorganisms and for cell regeneration. However, refractory wounds often occur in patients who are already immunologically suppressed and have a reduced inflammation response. This diminished immune response can no longer effectively fight off the primary wound bacteria and therefore the bacteria penetrate into the wound and form colonies that are organized as biofilms. Not only are these biofilms resistant to the defense system of the host but also they include planktonic cells or microcolonies.

In a preferred embodiment the preferred lactic acid bacteria, analogs, fragments, mutants, derivatives or combinations thereof preferably have at least one of the following features: a) thermal stability or stability after biological, chemical and/or physical treatment or b) ability to inhibit the formation of biofilm by Staphylococcus aureus and/or Pseudomonas aeruginosa. It was completely surprising that the lactic acid bacteria according to the invention would retain their ability to specifically bind Staphylococcus aureus and/or Pseudomonas aeruginosa even after biological, chemical and/or physical treatment.

Another property of the lactic acid bacteria according to the invention is the ability to inhibit the formation of a biofilm by Staphylococcus aureus and/or Pseudomonas aeruginosa. These bacteria form extremely tough biofilms which are resistant to ultrasound, detergents, proteases or heat and are also resistant to antimicrobial substances. The microorganisms according to the invention in particular have the property of inhibiting the formation of biofilm by Staphylococcus aureus and/or Pseudomonas aeruginosa. Because of the inhibition of the formation of the biofilm, these pathogenic bacteria can no longer colonize biological surfaces or inorganic surfaces and consequently can no longer cause diseases.

In the sense of the present invention, the phrase "inhibition the biofilm formation by Staphylococcus aureus and/or Pseudomonas aeruginosa" is therefore to be understood to refer in particular to the property of the lactic acid bacteria according to the invention to interact with Staphylococcus aureus and/or Pseudomonas aeruginosa, i.e., to bind to them or otherwise influence them in such a way that they can no longer form a biofilm.

According to a preferred embodiment, the microorganisms according to the invention may therefore have at least one of the stated properties, i.e., resistance to biological, chemical and/or physical treatment, heat resistance, capability for specific binding, coaggregation to Staphylococcus aureus and/or Pseudomonas aeruginosa. Preferred combinations of properties include, for example, resistance to biological, chemical and/or physical treatment, heat resistance and capability for binding to Staphylococcus aureus and/or Pseudomonas aeruginosa or resistance to biological, chemical and/or physical treatment, heat resistance and inhibition of biofilm formation by Staphylococcus aureus and/or Pseudomonas aeruginosa.

In the present case, as already stated, the expression "microorganism belonging to the genus or order of lactic acid bacteria" is also understood to include derivatives, mutants, analogs or fragments thereof which still have the characteristics and/or features or properties of the microorganisms according to the invention described here. The lactic acid bacteria according to the invention are preferably bacteria of the species Lactobacillus gasseri, Lactobacillus crispatus and Lactobacillus ingluviei.

Accordingly, "a mutant or a derivative" of the aforementioned microorganisms belonging to the genus of lactic acid bacteria, in particular a mutant or a derivative of the Lactobacilli sp., and having the same characteristics as those claimed for the lactic acid bacteria according to the invention in the present case and the same strains in particular is claimed. This would refer at least to the capability for specific coaggregation of at least one pathogenic microorganism selected from the group of *Staphylococcus aureus* and/or *Pseudomonas aeruginosa*. In addition, it is preferable to have at least one of the following features: (i) resistance of the capability for specific binding to a biological, chemical and/or physical treatment, in particular a heat treatment at more than 70° C. for at least 30 minutes; (ii) no binding to *Staphylococcus epidermidis* or other commensal skin microorganisms; (iii) capability for specific binding to at least one pathogenic, biofilm-forming microorganism; (iv) capability for inhibition of biofilm formation by *Staphylococcus aureus* or *Pseudomonas aeruginosa*; (v) existence of the specific binding at pH 3-8. Such preferred derivatives can be produced by genetic engineering, for example. The term "produced by genetic engineering" in the sense of the present invention includes in particular all methods with which those skilled in the art are familiar in the field of genetic engineering for modification of nucleic acids in vitro and in vivo so that genetic modifications can be induced by recombinant DNA technologies and genes can be modified.

Accordingly, the present invention also includes in particular fragments of the lactic acid bacteria according to the invention, which still have the properties of the lactic acid bacteria according to the invention. A "fragment" in the sense of the present invention is in particular a cellular component of the microorganisms according to the invention and preferably a part of the cell membrane. Those skilled in the art will be adequately familiar with methods of obtaining cell membrane fractions from the prior art.

The microorganisms according to the invention are preferably in isolated or purified form, where the term "isolated" means in particular that the lactic acid bacteria are derived from their culture medium—including for example, their natural medium. The term "purified" is not restricted to absolute purity.

It is preferable that, in addition to the microorganisms according to the invention in a viable form, inactive forms of the microorganisms according to the invention are also included within the scope of the present invention. The term "inactive form" here denotes inactivated or dead cells which are in particular no longer capable of forming colonies on culture plates. Those skilled in the art are familiar with suitable methods for inactivation (e.g., biological, chemical or physical inactivation methods). In the present case, however, the microorganisms may also be used in lyophilized form. Lyophilized cells can be induced to grow again after suitable culturing in a liquid or solid medium.

The terms "inactivated forms" or "inactive form" and "derivatives" or "analogs" or "mutants" also include in the present case cell and/or fermentation supernatants, lysates, fractions or extracts of the microorganisms according to the invention, where these lysates, fractions or extracts preferably have the properties of the lactic acid bacteria where "lysate"—as well as the term "extract"—refers in particular to a solution or suspension in an aqueous medium of the cells of the microorganism according to the invention and comprises, for example, macromolecules such as DNA, RNA, proteins, peptides, lipids, carbohydrates, etc. as well as cell detritus. The lysate preferably also includes the cell wall or cell wall constituents. Methods of producing lysates are sufficiently well known to those skilled in the art and includes for example, the use of a "French press" or enzymatic lysis, a ball mill with glass beads or iron beads. Cells can be broken open by enzymatic, physical or chemical methods. Examples of enzymatic cell lysis may include individual enzymes as well as enzyme cocktails for example, proteases, proteinase K, lipases, glycosidases; chemical lysis may be induced by ionophores, detergents such as SDS, acids or bases; physical methods may also be implemented by using high pressures such as the French press, osmolarities, temperatures or alternating between heat and cold. Furthermore, chemical, physical and enzymatic methods may of course be combined.

"Inactivated forms" or "inactive forms" and "derivatives" or "analogs" or "mutants" of the microorganisms according to the invention preferably have the same properties as the aforementioned strains. The "inactivated form" or the "inactive form" and "derivatives" or "analogs" preferably no longer have any metabolic activity.

Analogs of the microorganisms according to the invention are a form of the lysate or fragments. A fragment of the microorganisms according to the invention is a part of the cells such as the cell membrane, macromolecules such as DNA, RNA, proteins, peptides, lipids, carbohydrates, etc. as well as cell detritus. Those skilled in the art can supply the content for such terms as "analogs," "fragments," "derivatives" or "mutants" and they can interpret these terms in the sense of the present invention without any great technical effort. To provide mutants, derivatives, fragments or analogs of the preferred microorganisms, those skilled in the art may rely on the standard literature available to them, disclosing techniques that may be used to produce mutants, derivatives, fragments or analogs.

Mutants and/or genetically altered variants or derivatives are altered genetically for example, by recombinant DNA technologies (cloning, sequencing, transformation of recombinant nucleic acids) as well as physical mutagenesis, for example, by ultraviolet radiation but also due to chemical agents such as with ethyl methane sulfonate (EMS). Changes in the positive properties can be selected—either in a targeted manner or by evaluation of a plurality of mutants formed. Genetically altered mutants contain cells of the microorganisms according to the invention and entail recombinant nucleic acids in their bacterial chromosome and/or plasmids. Modifications due to point mutations may also have effects on the expression/transcription/translation as well as spontaneous mutations without any direct genetic manipulation.

Analogs or fragments may be thermally inactivated (dead) or lyophilized forms of the microorganisms according to the invention which retain or improve on their inventive properties, for example, by increasing the surface area. Even after lyophilization (freeze drying), cells may still viable under some circumstances. These cells may be inactivated through special storage processes at different temperatures. Inactivated cells may have intact or ruptured cell membranes for example, but they cannot have any metabolic activity. Methods of obtaining inactivated cells may include treating them with glass beads, for example, where the effect of the shearing forces between the cells and the glass beads cause the cells to rupture. Additional physical methods such as French press, high-pressure homogenization, ball mill or freeze-thaw processes and autoclaving also lead to inactivation and to fragments of the microorganisms according to the invention as well as UV irradiation, autolysis processes or special storage processes at different temperatures.

The term "*Lactobacillus* cells" in the sense of the present invention may also be used to refer to lactic acid bacteria or lactobacilli and also comprises microorganisms that require carbohydrates in particular glucose and lactose for fermentation of lactic acid and usually utilize the Embden-Meyerhof biosynthesis pathway. The *Lactobacillus* cells are taxonomically classified in the Lactobacteriaceae family. They are gram-positive, nonspore-forming and generally immobile. *Lactobacillus* cells live anaerobically but are aerotolerant although they do not contain any hemins (cytochrome, catalase) (Schleifer et al., *System. Appl. Microb.* 18, 461-467 (1995) or Ludwig et al., *System. Appl. Microb.* 15, 487-501 (1992). The *Lactobacillus* cells and/or the species can be determined on the basis of the carbohydrate utilization pattern in particular by means of the API test (Biomerieux Co.) and via 16sRNA sequencing. According to the invention this includes in particular species that are suitable for homofermentative lactic acid fermentation or heterofermentative lactic acid fermentation. Also preferable are those *Lactobacillus* cells selected from the group comprising *Lactobacillus lactis, Lactobacillus helveticus, Lactobacillus jensenii, Lactobacillus acidophilus, Lactobacillus bulgaricus, Lactobacillus amylovorus, Lactobacillus delbrueckii, Lactobacillus casei, Lactobacillus crispatus, Lactobacillus gasseri, Lactobacillus johnsonii, Lactobacillus paracasei, Lactobacillus pentosus, Lactobacillus rhamnosus, Lactobacillus curvatus* and *Lactobacillus plantarum* (all homofermentative), also *Lactobacillus brevis, Lactobacillus buchneri, Lactobacillus fructivorans, Lactobacillus hilgardii, Lactobacillus fermentum, Lactobacillus reuteri, Lactobacillus viridescens* as well as *Bifidobacterium bifidum* (all heterofermentative).

In a preferred embodiment, the microorganism according to the present invention is selected from *Lactobacillus gasseri, lactobacillus gasseri, Lactobacillus gasseri, Lactobacillus crispatus, Lactobacillus crispatus, Lactobacillus crispatus, Lactobacillus crispatus, Lactobacillus crispatus, Lactobacillus crispatus* and *Lactobacillus ingluviei*, each deposited with the German Collection for Microorganisms and Cell Cultures (DSMZ) in Braunschweig under the deposition numbers DSM 25906, DSM 25907, DSM 25908, DSMZ 25909, DSM 25910, DSM 25911, DSM 2591, DSM 25913, DSM 25914 and DSMZ 25915. The aforementioned DSMZ depositions were made in accordance with the Budapest Treaty regarding international recognition of the deposition of microorganisms for the purpose of patent deposition.

As explained further above, the present invention also relates to compositions preferably containing viable microorganisms or an analog, mutant, derivative or fragment thereof as well as preferably at least one vehicle or excipient which is selected from at least one of the following: a cosmetically acceptable vehicle or excipient, a pharmaceutically acceptable vehicle or excipient or a dermatologically acceptable vehicle or excipient.

The term "composition" in the sense of the present invention is understood to include in particular any composition having at least one microorganism according to the invention or a fragment, derivative, analog or mutant thereof as well as optionally other ingredients such as vehicles or excipients or optionally other active ingredients and salts. Cosmetically, pharmaceutically or dermatologically acceptable excipients, vehicles or additives are understood to include any substances that are conventionally used in the cosmetic, pharmaceutical or dental areas in order to administer, to use or to activate, cosmetically or pharmaceutically, an active ingredient or composition, i.e., in the present case, at least one microorganism or analog or derivative or mutant or fragment thereof.

It is preferable for the composition to contain not only one of the microorganisms according to the invention or an analog, mutant, derivative or fragment thereof, but also to contain a mixture of microorganisms according to the invention or a mixture of the analogs, derivatives, mutants or fragments or a mixture of the microorganisms according to the invention and fragments, derivatives, mutants or analogs thereof.

The composition may preferably be in an solid or liquid or viscous form or an aerosol and may be used, for example, in the form of powders, tablets, solutions, granules, suspensions, emulsions, capsules, pastes, gels, sprays, etc., i.e., in any form suitable for administration. It is also preferable if the composition comprises additional probiotics, antiseptics or other antibacterial substances and, preferably but optionally, saccharides and preservatives, flavorings, sweeteners, vitamins, minerals, etc. The document EP 2 133 414 A1 lists a number of ingredients that an be used for preferred compositions; reference is made explicitly to this publication. Furthermore, fillers, flow control agents, rheology modifiers, softeners, stabilizers, initiators or reactively crosslinked monomers, for example, methacrylates may be present in a preferred composition.

The composition according to the invention is used in particular for use in physical hygiene, physical therapy and prophylaxis and contains at least one microorganism according to the invention or a derivative, mutant, fragment or analog thereof.

The composition and/or microorganism may also be used as a disinfectant for example, as a surface disinfectant such as in particular as a cleaning solution for contact lenses.

The dosage and the administration for using the composition according to the invention depend on the respective use and the respective patient—in particular the age, weight, general health, etc.—and are within the capabilities and assessment of those skilled in the art who will be using the composition.

The composition according to the invention may be a cosmetic product, a medicinal product or a pharmaceutical product. The composition preferably contains the lactic acid bacteria in an amount by weight of 0.001% by weight to 10% by weight, preferably 0.005% by weight to 5% by weight, especially preferably 0.01% by weight to 3% by weight. It was completely surprising that the use of an amount of 0.001% by weight to 10% by weight in particular would result in decomposition being usable for a longer period of time, i.e., remaining stable. If the lactic acid bacteria are used in an amount of 0.005% by weight to 5% by weight, this surprisingly results in a positive effect on the rheological properties of the composition and results in the composition having a lower viscosity and thus being distributed better on the skin or being easier to introduce into the oral cavity. Use of the lactic acid bacteria in an amount by weight of 0.01% by weight to 3% by weight has surprisingly resulted in the components of the composition bonding to one another better and the possibility of supplying a homogeneous composition in a reduced working time, which in turn leads to a reduction in the production costs. It is self-evident, however, that other amounts differing from those specified herein may also be used for specific applications.

As explained above, according to a preferred embodiment the composition and/or the microorganism may be used in the field of physical hygiene to aggregate, i.e., to bind the aforementioned pathogenic microorganisms. These coaggregates can then be removed easily by rinsing them off, for example, in the case of a suspension in particular, so that a reduction in the number of pathogenic microorganisms is advantageously achieved. The lactic acid bacteria and/or a composition containing them may therefore be used in various ways for this purpose. For example, they may be used in shower gels, shower lotions, body lotions, liquid soaps, soaps, shower oils or disinfection solutions, filter systems in respiratory equipment, nose sprays, cleaning solutions for contact lenses, towels or cleaning towels. The present invention therefore also relates to all products which are used in the field of physical hygiene and medical products and prevention and which contain the lactic acid bacteria according to the invention. The embodiments described above also apply accordingly for the field of treatment, therapy and prevention in mammals. The microorganisms and/or a composition containing them may therefore be used in a variety of ways.

It is preferable in particular if the composition according to the invention and/or the microorganism according to the invention is/are used to produce a pharmaceutical drug, for treatment or prevention of diabetes mellitus, skin diseases, skin injuries, toxic shock syndrome, staphylococcal scaled skin syndrome as well as the toxic infections caused by enterotoxins, furuncles, carbuncles, sinusitis, osteomyelitis such as sepsis and subsequently a meningitis and/or myocarditis and pericarditis caused by *Staphylococcus aureus* and pneumonia with cystic fibrosis, urinary tract infections, enterocolitis, meningitis, otitis externa, infections on burns due to *Pseudomonas aeruginosa*.

Agents are made available through the microorganisms according to the invention and the compositions containing them with which these diseases can be treated and/or prevented advantageously. The microorganisms and/or the compositions containing them may be used in human and veterinary medicine in particular, as indicated above, in the dog, monkey, cat, horse and rodents (hares, rabbits, hamsters, guinea pigs) and commercial animals such as chickens, pigs and cattle, sheep, goats and other domestic and commercial animals.

The composition according to the invention and/or the microorganisms—or fragments, derivatives or mutants thereof—may be used in particular as a food additive, as a hygiene product, as a hygiene product containing the microorganism or as a pharmaceutical preparation. Such hygiene products may also be in the form of kits for example, which may also contain the microorganisms according to the invention or compositions containing same in addition to physical hygiene devices or equipment, rinses, pastes, etc.

The present invention also relates to a method for identifying and/or selection of a microorganism of the genus *Lactobacillus* sp. having the properties according to the invention, wherein the method comprises at least the following steps: a) incubating a batch of a pathogenic microorganism selected from *Staphylococcus aureus* and/or *Pseudomonas aeruginosa* for the development of a biofilm, b) adding the microorganism of the *Lactobacillus* genus to be investigated and incubating the batch to form the specific binding between the pathogenic microorganism and the microorganism of the *Lactobacillus* genus to be investigated, c) separating the unbound microorganisms of the *Lactobacillus* genus by removing the supernatant and d) determining the biofilm with regard to bound and aggregated microorganisms of the *Lactobacillus* genus.

In a preferred embodiment, the method according to the invention also comprises the step of investigating the inhibition of biofilm formation by pathogenic microorganisms. The microorganisms of the *Lactobacillus* genus to be investigated were added here during the incubation of the biofilm-forming pathogenic microorganism. After removing the unbound cells, the formation of biofilm is preferably quantified by measuring the optical density, in particular after crystal violet staining in comparison with controls without adding the microorganisms to be tested.

It is self-evident that the features mentioned above and those yet to be described below may be used not only in the particular combination given but also alone without going beyond the scope of the present invention.

The teaching according to the present patent application is characterized by the following features:

Departure from what is customary in the prior art,
New statement of object,
Existence of an urgent need for a solution to the problem which has not been solved for a long time but is solved by the invention,
Previous unsuccessful efforts on the part of the technical world,
The simplicity of the solution suggests an inventive step, in particular since it replaces more complex teachings,
Development of the scientific technique went in a different direction,
An accomplishment that leads to further development,
Faulty concepts in the technical world concerning the solution to the corresponding problem (prejudice against technical progress, for example: improvement, increased performance, reduction in cost, time saving, material, working steps, costs or difficult to acquire raw materials, increased reliability, elimination of defects, increasing quality, freedom from maintenance, greater efficacy, higher yield, increase in technical possibilities, providing another means, opening a second pathway, opening a new territory, first solution to a problem, reserve means, alternatives, possibility of economization, automation or miniaturization or enrichment of the drug resources,
A lucky happenstance because one specific possibility has been selected from a variety of possibilities, the results could not have been predicted, so this is a lucky happenstance that can be patented,
Mistakes in the technical literature and/or very contradictory presentation of the subject matter of the invention,
New field of technology,
Combination invention, i.e., multiple known elements are combined to yield a combination that has a surprising effect,
Issuance of licenses,
Praise for the technical world, and
Economic success.

In particular the advantageous embodiments of the invention have at least one or more of the aforementioned advantages.

DESCRIPTION OF THE FIGURES

The invention will be explained below as an example on the basis of figures and examples but without being limited to them.

FIG. 4: The microscopic control of the specific binding of an exemplary embodiment of a microorganism according to the invention (DSM 25909, DSM 25910, DSM 25911) to *Pseudomonas aeruginosa* cells after coaggregation and the *Lactobacillus* strains according to the invention and the target strain separately. Micrograph (phase contrast, magnification 1000×).

FIG. 5: The macroscopic control of the specific binding of an exemplary embodiment of a microorganism according to the invention (DSM 25906, DSM 25907, DSM 25908) to *Staphylococcus aureus* cells after coaggregation and the *Lactobacillus* strains according to the invention and the target strain separately in a photo documentation system.

FIG. 6: The microscopic control of the specific binding of an exemplary embodiment of a microorganism according to the invention (DSM 25906, DSM 25907, DSM 25908) to *Staphylococcus aureus* cells after coaggregation and the *Lactobacillus* strains according to the invention and the target strain separately. Micrograph (phase contrast, magnification 1000×).

DETAILED DESCRIPTION OF THE EXEMPLARY EMBODIMENTS

Example 1

For identification and selection of microorganisms according to the invention, various strains from a *Lactobacillus* strain bank were tested by a four-step screening process in which they were first screened with regard to the ability to bind to the pathogenic skin microorganisms (hereinafter also referred to as the "target microorganism) (binding assay) and then the strains identified in the first step were tested in a coaggregation assay in a microtiter plate scale, where coaggregation with the respective target organism was measured qualitatively using a binocular stereo microscope. Furthermore, the intensity of the coaggregation and the stability of the binding to the target microorganism as well as the capacity for prevention of a biofilm were investigated, which ultimately lead to the exemplary microorganisms identified according to the invention (*Lactobacillus*).

Binding Assay

Figure 1:
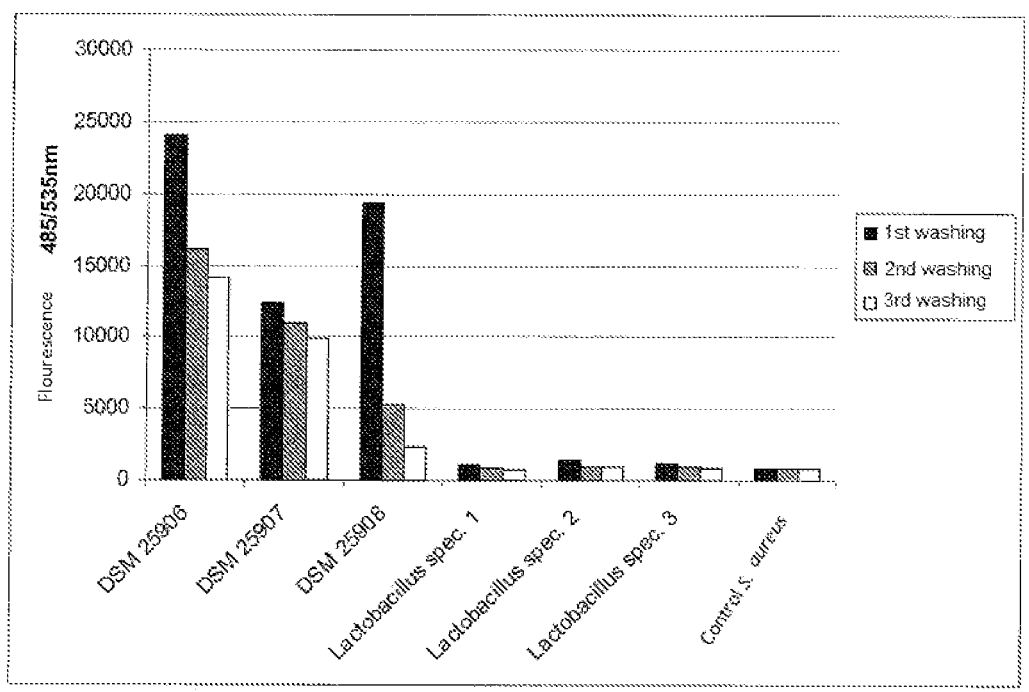
FIG. 1: The specific binding and/or aggregation of one exemplary embodiment of the microorganisms according to the invention (DSM 25906, DSM 25907, DSM 25908) to a biofilm formed by *Staphylococcus aureus* (binding assay) after washing the unbound cells three times and, for comparison with that, additional *Lactobacillus* strains that are not according to the invention and are capable of binding to *Staphylococcus aureus* (*Lactobacillus* species 1 and *Lactobacillus* species 2 and *Lactobacillus* species 3); specific quantification of the binding and/or aggregation of CFDA-labeled *Lactobacillus* strains according to the invention to the biofilm in 96-well microtiter plates based on fluorescence measurement (485/535 nm).
Figure 2:
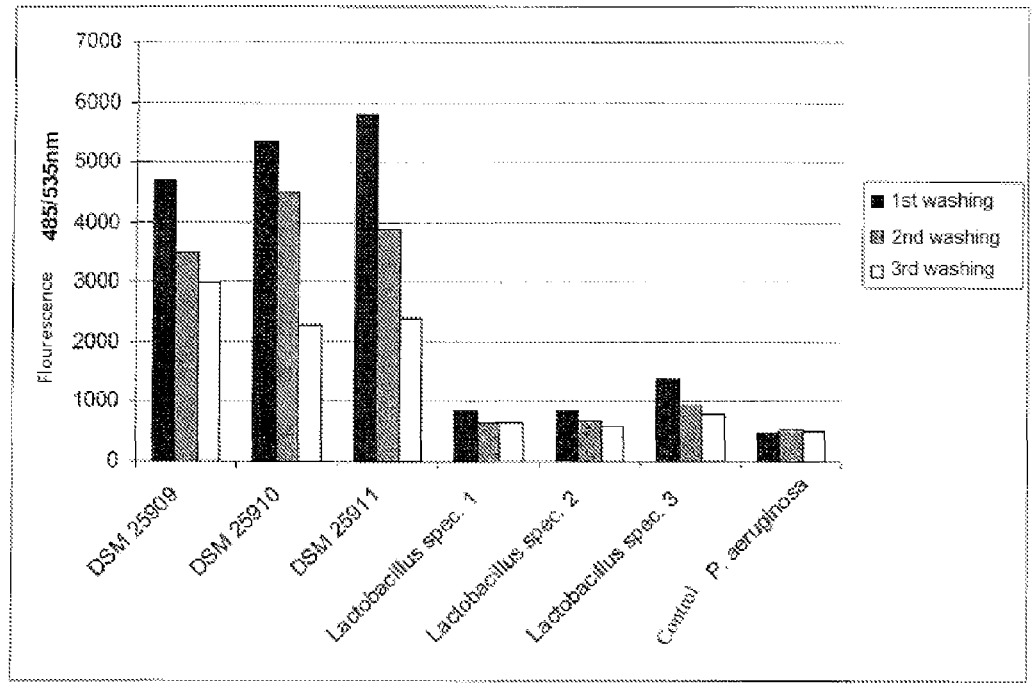
FIG. 2: The specific binding and/or aggregation of exemplary embodiment of the microorganisms according to the invention (DSM 25909, DSM 25910, DSM 25911) to biofilm formed by *Pseudomonas aeruginosa* (binding assay) after washing out the unbound cells three times and in comparison with that additional *Lactobacillus* strains that are not according to the invention and are not capable of binding to *Pseudomonas aeruginosa* (*Lactobacillus* species 1 and *Lactobacillus* species 2 and *Lactobacillus* species 3); specific quantification of the binding and/or aggregation of CFDA-labeled *Lactobacillus* strains according to the invention to the biofilm in 96-well microtiter plates based on fluorescence measurements (485/535 nm).

To be able to quantify the binding activity of selected *Lactobacillus* strains, a binding assay was established, permitting quantitative detection of the binding of *Lactobacillus* strains to pathogenic microorganisms in a 96-well plate. The binding activity of the *Lactobacillus* cells with the target organism correlates with the coaggregation activity and/or coaggregation capability. This was tested experimentally. In this regard, FIG. 2 shows an example of the coaggregation of the *Lactobacillus* strains DSM 25909, DSM 25910, DSM 25911 and *Pseudomonas aeruginosa* DSM 22644, and FIG. 1 shows *Lactobacillus* strains DSM 25906, DSM 25907, DSM 25908 and *Staphylococcus aureus* DSM 22644.

The measurement method is based on the specific binding of the strains according to the invention to a target strain bound in a biofilm. Defined amounts of the strains according to the invention were labeled with a fluorescent dye (CFDA solution, Invitrogen) and were mixed with a defined amount of target organisms bound to a biofilm for the assay. The persistence of the bound strains according to the invention on the target strain is measured using a fluorescence photometer after washing several times.

To perform these experiments, the target microorganisms *Pseudomonas aeruginosa* (DSMZ 22644) and *Staphylococcus aureus* (DSMZ 18587) was cultured according to standard methods using TSB (trypticase soy broth) for *Pseudomonas aeruginosa* and TSY (trypticase soy yeast extract medium) for *Staphylococcus aureus*.

The *Lactobacillus* strains were cultured anaerobically in MRS medium at 37° C. (de Man et al., 1960).

For workup of the target microorganisms, the cells were harvested after reaching the incipient steady-state growth phase, washed three times with phosphate-buffered saline (PBS, pH 7.4) and placed in PBS. Then 100 µL of the suspension was placed in each well of a 96-well microtiter plate.

During a 6-hour aerobic incubation, a biofilm was formed by the target strains. After incubation unbound cells were removed by washing three times with phosphate-buffered saline (PBS, pH 7.4).

For workup of the *Lactobacillus* strains, they were harvested and washed three times with PBS after culturing for 24 hours, placed in PBS and fluorescence-labeled by adding CFDA solution (Invitrogen).

To perform the binding assay, 100 µL of the *Lactobacillus* suspension was added to the target strains bound in a biofilm in each well. Control batches without the addition of the *Lactobacillus* suspension were carried in parallel. After incubating for 1 hour at 30° C. in an incubator, the unbound cells were separated and washed three times with PBS. After each washing step the fluorescence was measured in the fluorescence plate photometer (Em 485 nm/Ex 535 nm).

The increase in fluorescence (Em 485 nm/Ex 535 nm) in the batch containing *Lactobacillus* strains in comparison with the control without *Lactobacillus* cells correlated with the amount of biofilm-bound *Lactobacillus* cells. The measured fluorescence after binding of the *Lactobacillus* cells corresponded to the binding intensity. The higher this value, the better the binding of the labeled *Lactobacillus* cells to the target strains bound in the biofilm and the greater the binding activity of the *Lactobacillus* cells tested.

The experiments have shown that after removal of the unbound cells, the tested *Lactobacillus* strains led to an increase in fluorescence by a factor of 3 to 17 after three washings due to the binding of the labeled *Lactobacillus* cells, which are bound in the biofilm, for the target organism/target strain *Pseudomonas aeruginosa* and/or *Staphylococcus aureus* in the binding assay. FIG. 2 shows the results of the binding assay for *Lactobacillus* DSM 25909, DSM 25910 and DSM 25911 with *Pseudomonas aeruginosa* and FIG. 1 for DSM 25906, DSM 25907 and DSM 25908 with *Staphylococcus aureus* as exemplary for the microorganisms according to the invention. In addition, for comparison purposes, FIGS. 1 and 2 also show the data on *Lactobacillus* strains not according to the present invention (*Lactobacillus* species 1 and 2) which are not capable of specific binding for the target organism.

Example 2

Coaggregation Assay

The following verification in a volume of 0.8 mL and/or in a 24-well plate is used to illustrate the coaggregation activity of selected *Lactobacillus* strains.

In this method, the coaggregation behavior of the Lactobacilli and of the target strain are considered separately, and finally, the coaggregation of *Lactobacillus* and the target strain brought together in a mixture is considered. This analysis is performed macroscopically by using photographs of the 24-well plate as well as microscopically.

To perform these tests the target microorganism *Pseudomonas aeruginosa* (DSMZ 22644) and *Staphylococcus aureus* (DSMZ 18587) was cultured according to standard protocols using TSB (trypticase soy broth) for *Pseudomonas aeruginosa* and TSY (trypticase soy yeast extract medium).

The *Lactobacillus* strains were cultured anaerobically at 37° C. in MRS medium (de Man et al., 1960).

For workup of the target microorganisms, the cells were harvested after 16 hours, washed three times with phosphate-buffered saline (PBS, pH 7.4) and adjusted to $OD_{600}=4$.

For workup of the *Lactobacillus* strains, they were harvested after 16 hours, washed twice with PBS and then placed in a volume of PBS and adjusted to an $OD_{600}=8$ accordingly.

To perform the coaggregation assay, 400 µL suspension of the labeled target microorganism was placed in each well together with 400 µL *Lactobacillus* suspension in a 24-well plate. Control batches with 400 µL of the respective target organism plus 400 µL PBS (control 1) or 400 µL of the respective *Lactobacillus* suspension plus 400 µL PBS (control 2) were prepared in parallel. After incubating for 30 minutes at 25° C. on a desktop agitator, the batches were observed macroscopically by means of a photo documentation system as well as microscopically by transferring 3 µL from the center of each well to a microscope slide.

For quantification of the coaggregation, the resulting coaggregates were separated by centrifugation (10 sec, 300 g). Then 100 µL of the supernatant was transferred to a 96-well flat-bottom plate and the optical density was measured at 600 nm in the plate photometer.

The following formula was used for a percentage calculation of the coaggregation activity:

$$\% \text{ Aggregation} = \frac{(OD_{\text{target strain separately}} + OD_{\text{Lactobacillus separately}}) - OD_{\text{coaggregation}}}{OD_{\text{target strain separately}} + OD_{\text{Lactobacillus separately}}} \times 100$$

The optical density of the target microorganism as well as that of the *Lactobacillus* strains and that of the coaggregation batch were used for calculation of the percentage coaggregation activity.

Figure 3:
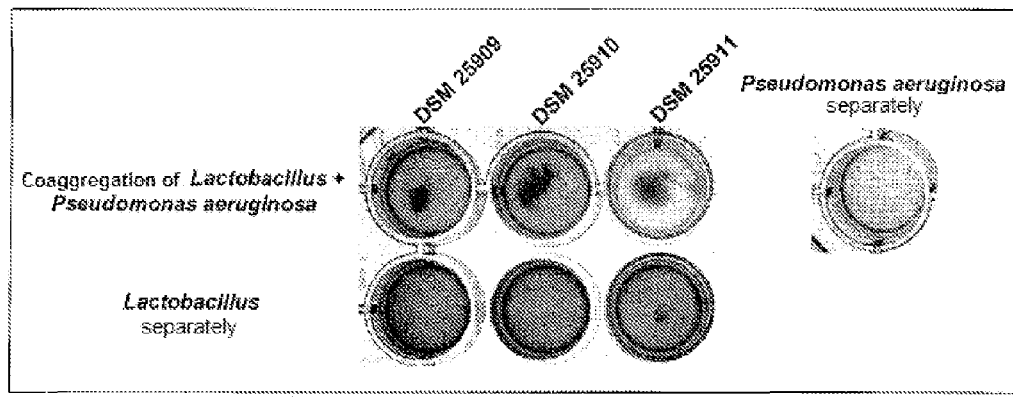
FIG. 3: The macroscopic control of the specific binding of an exemplary embodiment of a microorganism according to the invention (DSM 25909, DSM 25910, DSM 25911) to *Pseudomonas aeruginosa* cells after coaggregation and the *Lactobacillus* strains according to the invention and the target strain separately in a photo documentation system.

Experiments have shown that the selected *Lactobacillus* strains result in lumps (aggregates) in the mixture for the target microorganism/target strain *Staphylococcus aureus* and/or *Pseudomonas aeruginosa* in the coaggregation, these aggregates being visible macroscopically due to dark areas in the well. No aggregates are formed in the wells containing the target strains and/or the *Lactobacillus* strains according to the invention separately. This is visible due to the absence of dark areas formed in the well. FIG. 5 shows the macroscopic results in the coaggregation batch for the selected *Lactobacillus* strains for the target microorganism/target strain *Staphylococcus aureus* and FIG. 3 shows the results for the target strain *Pseudomonas aeruginosa*. In the microscopic observation, the unambiguous affinities for the respective target strains which lead to different aggregate sizes in the microscopic consideration of coaggregation are found in the microscopic observation of all the *Lactobacillus* strains according to the invention. FIG. 4 shows the microscopic results in the coaggregation batch for the selected *Lactobacillus* strains for the target microorganisms/target strain *Staphylococcus aureus* in FIG. 6 and/or for *Pseudomonas aeruginosa*.

Example 3

Furthermore, experiments were conducted to show the influence of proteases on the *Lactobacillus* strains according to the invention and their aggregation properties on the target microorganisms.

The *Lactobacillus* strains according to the invention and the target strains were therefore processed as described in Example 2.

The *Lactobacillus* strains according to the invention were treated with proteases, shown here on the example of protease, trypsin. After processing the *Lactobacillus* strains, they were treated with trypsin at 37° C. for 60 minutes (12.4 units/mg, Sigma). Then the cells were again washed twice with PBS and the aggregation properties were quantified as described in Example 2.

Figure 9:
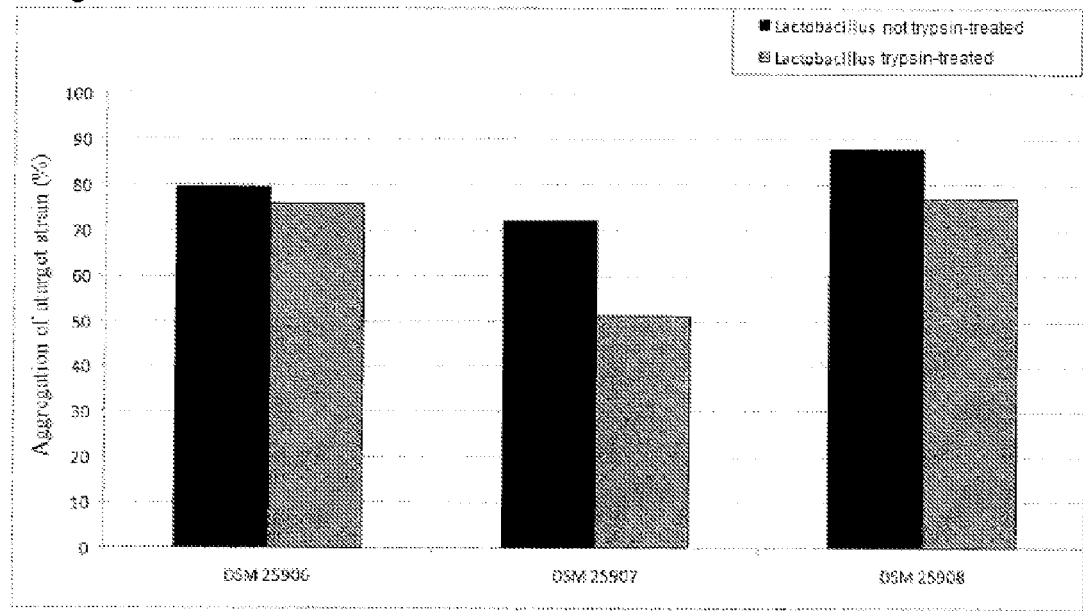
FIG. 9: The specific aggregation of an exemplary embodiment of the microorganisms according to the invention (DSM 25906, DSM 25907, DSM 25908) with and without trypsin treatment of *Staphylococcus aureus* (DSM 18587) in the coaggregation assay; specific quantification of the aggregation by measurement of the optical density at 600 nm of the target microorganism separately and that of the *Lactobacillus* strains separately and that of the coaggregation batch.

These experiments have shown that after treatment with protease, the *Lactobacillus* strains according to the invention have 50-76% aggregation in the coaggregation assay of the target microorganism for the target microorganism/target strain *Pseudomonas aeruginosa* and/or *Staphylococcus aureus*. As an example the microorganisms according to the invention, FIG. 9 shows the results of the coaggregation assay for *Lactobacillus* DSM 25906, DSM 25907 and DSM 25908 with and without trypsin treatment with *Staphylococcus aureus*.

Example 4

Experiments were conducted with additional commensal skin microorganisms to show the specificity of the aggregation properties of the *Lactobacillus* strains according to the invention against the target microorganisms. *Staphylococcus epidermides* (DSM 20044), *Corynebacterium jeikeium* (DSM 7171) and *Micrococcus luteus* (DSM 20030) were selected. The *Lactobacillus* strains according to the invention and the target microorganisms were cultured and worked up as described in Example 2.

To perform these tests, all the target microorganisms to be tested, i.e., *Pseudomonas aeruginosa* (DSMZ 22644), *Staphylococcus aureus* (DSMZ 18587), *Staphylococcus epidermides* (DSM 20044), *Corynebacterium jeikeium* (DSM 7171) and *Micrococcus luteus* (DSM 20030) were cultured according to standard protocols, using TSB (trypticase soy broth) for *Pseudomonas aeruginosa* and TSY (trypticase soy yeast extract medium) for *Staphylococcus aureus* (DSMZ 18587), *Staphylococcus epidermides* (DSM 20044), *Corynebacterium jeikeium* (DSM 7171) and *Micrococcus luteus* (DSM 20030).

The target strains and C aggregation assay were performed as described in Example 2.

Figure 7:
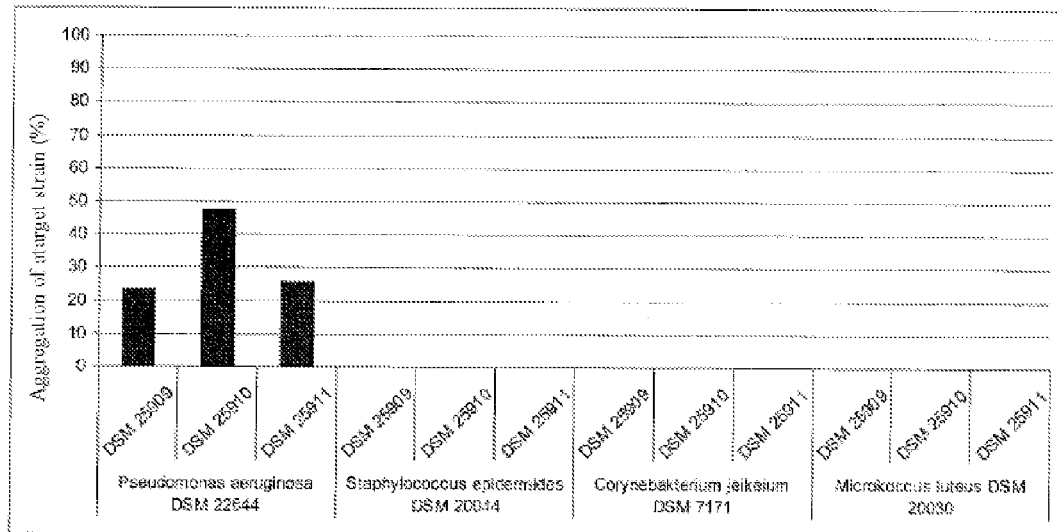
FIG. 7: The specific aggregation of an exemplary embodiment of the microorganisms according to the invention (DSM 25909, DSM 25910, DSM 25911) of *Pseudomonas aeruginosa* (DSM 22644), *Staphylococcus epidermides* (DSM 20044), *Corynebacterium jeikeium* (DSM 7171) and *Micrococcus luteus* (DSM 20030) in coaggregation assay; specific quantification of the aggregation by measurement of the optical density at 600 nm of the target microorganism separately as well as that of the *Lactobacillus* strains separately and that of the coaggregation batch.
Figure 8:
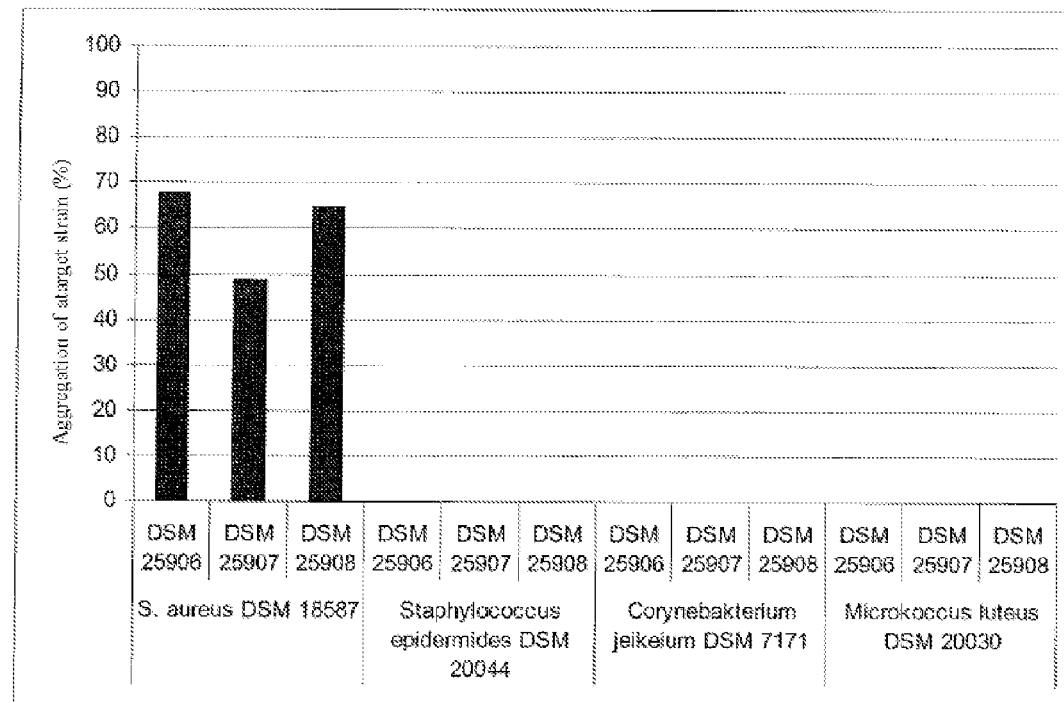
FIG. 8: The specific aggregation of an exemplary embodiment of the microorganisms according to the invention (DSM 25906, DSM 25907, DSM 25908) of *Staphylococcus aureus* (DSM 18587), *Staphylococcus epidermides* (DSM 20044), *Corynebacterium jeikeium* (DSM 7171) and *Micrococcus luteus* (DSM 20030) in coaggregation assay; specific quantification of the aggregation by measurement of the optical density at 600 nm of the target microorganism separately as well as that of the *Lactobacillus* strains separately and that of the coaggregation batch.

Experiments have shown that there is no aggregation with the additional target strains investigated by the *Lactobacillus* strains according to the invention but instead these were very specific properties. FIG. 8 shows the results of the coaggregation assay for *Lactobacillus* DSM 25906, DSM 25907 and DSM 25908 with *Staphylococcus aureus* for the microorganisms according to the invention and FIG. 7 shows the results for *Lactobacillus* DSM 25909, DSM 25910 and DSM 25911 with *Pseudomonas aeruginosa*.

Example 5

Furthermore, tests were conducted with other microorganisms of the same genus and species of skin microorganisms to determine the specificity of the binding properties and/or aggregation properties of the *Lactobacillus* strains according to the invention against the target microorganisms of the same genus and species. For this purpose, *Staphylococcus aureus* (DSMZ 20232) was selected to manifest its aggregation properties with the tests with the target microorganisms.

The *Lactobacillus* strains according to the invention and the target microorganisms were therefore cultured and worked up as described in Example 2.

To perform these tests, all the target microorganisms to be investigated, namely in this example *Staphylococcus aureus* (DSMZ 18587) and *Staphylococcus aureus* (DSMZ 20232) were cultured according to standard protocols using TSY (trypticase soy yeast extract medium).

The target strains were processed and the coaggregation assay was performed as described in Example 2.

Figure 10:
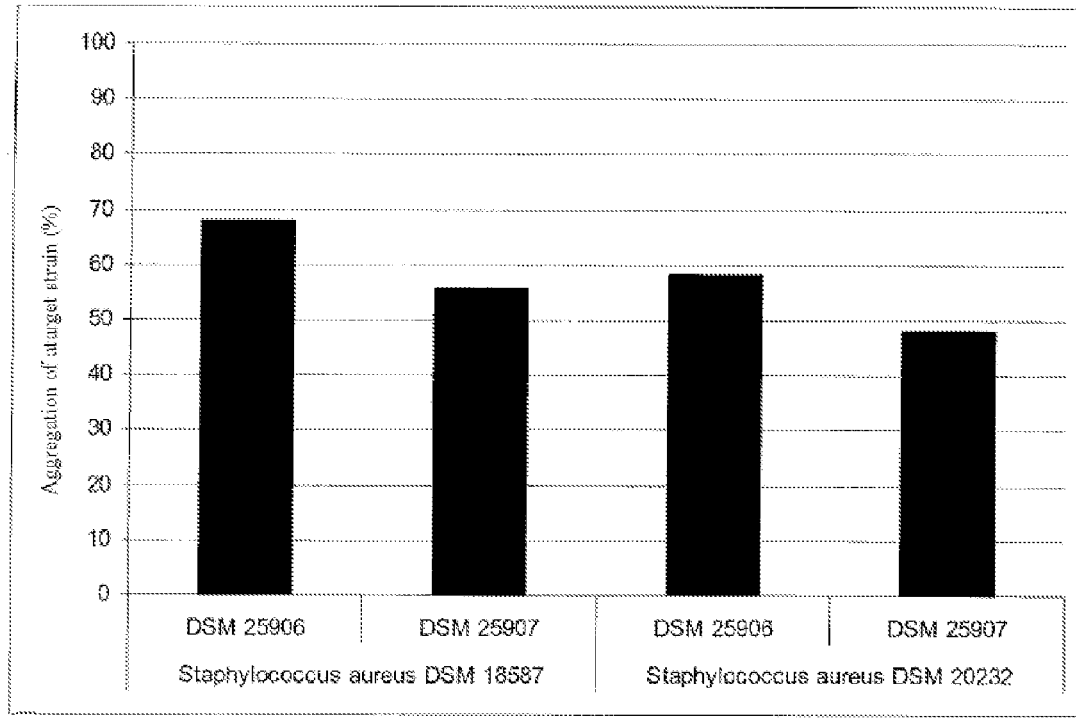
FIG. 10: The specific aggregation of an exemplary embodiment of the microorganisms according to the invention (DSM 25906 and DSM 25907) of *Staphylococcus aureus* (DSM 18587) and *Staphylococcus aureus* (DSM 20232) in the coaggregation assay; specific quantification of the aggregation by measurement of the optical density at 600 nm of the target microorganism separately and that of the *Lactobacillus* strains separately and that of the coaggregation batch.

These experiments have shown that other microorganisms of the same genus and species are also capable of binding and/or aggregation due to the *Lactobacillus* strains according to the invention. FIG. 10 shows the results of the coaggregation assay for *Lactobacillus* DSM 25906 and DSM 25907 with *Staphylococcus aureus* DSMZ 18587 and DSMZ 20232 being used as examples of the microorganisms according to the invention.

Example 6

Inhibition of Biofilm

For identification and selection of microorganisms according to the invention, various strains from a *Lactobacillus* databank were tested in a screening method on a microtiter plate scale. The purpose of the screening was to determine the properties of the pathogenic skin microorganisms (hereinafter also referred to as "target microorganisms") in preventing the formation of a biofilm. The intensity of the biofilm-preventing properties were related quantitatively to the uninfluenced formation of biofilm of the target microorganisms and were analyzed, ultimately leading to the identified microorganisms according to the invention (*Lactobacillus*).

To investigate their effect on the formation of biofilm by the pathogenic target microorganisms *Staphylococcus aureus* (DSM 18587) or *Pseudomonas aeruginosa* (DSM 22644), the *Lactobacillus* strains and/or fractions thereof were added directly to the target microorganism at the start of formation of the biofilm and were incubated for up to 6 hours. After removing the cells that were not bound and washing the biofilms twice with PBS, the biofilms were quantified by measuring the optical density after crystal violet staining of the entire batch.

To perform these tests the target strains were cultured according to a standard protocol as described further above and the *Lactobacillus* strains were cultured anaerobically in MRS medium.

For workup of the *Lactobacillus* strains, they were washed twice with PBS after culturing and then placed in PBS.

Some of the *Lactobacillus* strains were heat-inactivated by pasteurizing for 30 minutes at 70° C. after washing with PBS.

In addition, some of the heat-inactivated *Lactobacillus* strains were used to obtain the supernatants after washing with PBS. This was done by centrifugation of the suspension and then using the supernatants.

For workup of the target strains, they were cultured and harvested until achieving the mean exponential growth phase and then were adjusted to $OD_{600\ nm\ (mL-1)}=3.5$, washed twice with PBS and placed in PBS.

Figure 11:
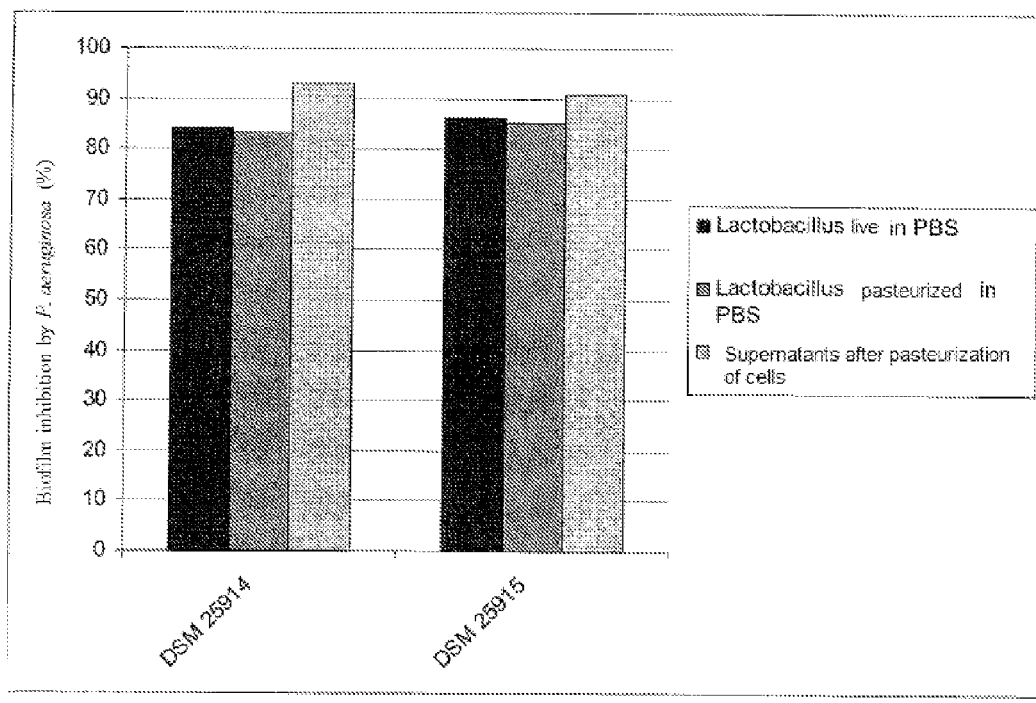
FIG. 11: Inhibition of the biofilm formation of an exemplary embodiment of the microorganisms according to the invention (DSM 25914 and DSM 25915) of the biofilm formed by *Staphylococcus aureus* after 6 hours of incubation by *Lactobacillus* suspension washed in PBS, heat-inactivated *Lactobacillus* suspension and supernatants of the heat-inactivated *Lactobacillus* suspension; quantification of the biofilm by crystal violet staining in a 96-well microtiter plate over measurement of the optical density at 590 nm.
Figure 12:
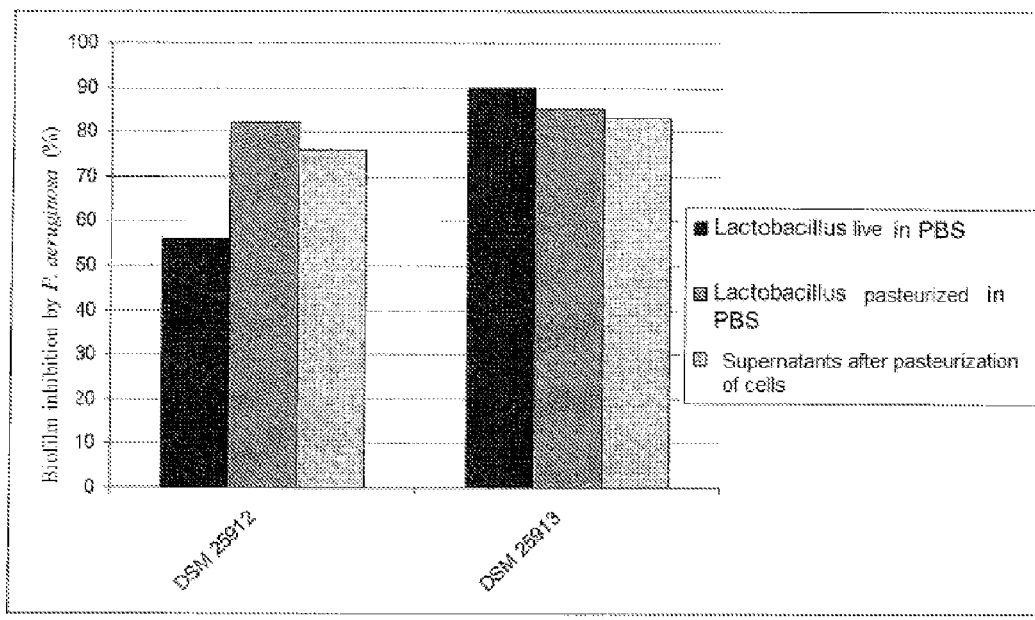
FIG. 12: Inhibition of the biofilm formation of an exemplary embodiment of the microorganisms according to the invention (DSM 25912 and DSM 25913) of the biofilm formed by *Pseudomonas aeruginosa* after 6 hours of incubation by *Lactobacillus* suspension washed in PBS, heat-inactivated *Lactobacillus* suspension and supernatants of the heat-inactivated *Lactobacillus* suspension; quantification of the biofilm by crystal violet staining in a 96-well microtiter plate over measurement of the optical density at 590 nm.

To perform the biofilm formation assay, the *Lactobacillus* strains were added directly to the target microorganism at the start of formation of the biofilm and were incubated anaerobically at 37° C. for 6 hours. Control batches without the addition of the *Lactobacillus* suspension were carried in parallel. After removing the planktonic cells and washing the biofilms, the biofilms were quantified by crystal violet staining (0.1%, Merck) of the bound target microorganism with and without *Lactobacillus* and/or *Lactobacillus* fractions. To do so, the bound cells of the respective batches were dissolved by means of acetic acid after crystal violet staining and were then placed in suspension and measured at an optical density of 590 nm. The reduction in optical density at 590 nm in comparison with the control of the target microorganism without lactobacilli correlated with the intensity of hindrance of the biofilm. This reduction is represented as the percentage inhibition of biofilm formation in relation to the target microorganism without lactobacilli. As exemplary of the microorganisms according to the invention, FIG. 11 shows the result of the biofilm inhibition of *Staphylococcus aureus* by *Lactobacillus* DSM 25914 and DSM 25915 and by *Pseudomonas aeruginosa* by DSM 25912 and DSM 25913, as shown in FIG. 12. Experiments have shown that this leads to 56-93% inhibition of the formation of biofilm by the *Lactobacillus* strains according to the invention, with and without inactivation of the metabolic activities of the *Lactobacillus* strains and/or their fractions of *Staphylococcus aureus* and/or *Pseudomonas aeruginosa*.

These experiments and examples have shown only a selection of preferred microorganisms wherein the joint advantageous properties have been confirmed experimentally for all the preferred microorganisms. Those skilled in the art will learn from the examples and the figures how to proceed in reproducing the invention and, for example, reproducing the shared advantageous properties of the preferred microorganisms.

REFERENCES

Davies C E, Hill K E, Wilson M J, Stephens P, Hill C M, Harding K G and Thomas D W (2004) Use of 16S ribosomal DNA PCR and denaturing gradient gel electrophoresis for analysis of the microfloras of healing and nonhealing chronic venous leg ulcers, *J Clin Microbiol* 42, 3549-57.

Fux, C A, Costerton, J W, Stewart, P S, Stoodley P (2005) Survival strategies of infectious biofilms. *Trends in Microbiology* 13, 34-40.

James T J, Hughes M A, Cherry G W, Taylor R P. Evidence of oxidative stress in chronic venous ulcers. *Wound Repair Regen* 2003; 11(3): 172-6.

James G A, Swogger E, Wolcott R, Pulcini E, Secor P, Sestrich J, Costerton J W, Stewart P S (2008) Biofilms in chronic wounds. Wound Repair Regen 16, 37-44.

Kirketerp-Møller K, Jensen P Ø, Fazli M, Madsen K G, Pedersen J, Moser, C, Tolker-Nielsen, T. Høiby N, Givskov M, and Bjarnsholt T (2008) Distribution, Organization, and Ecology of Bacteria in Chronic Wounds, *J Clin Microbiol* 46, 2717-2722.

Mast B A, Schultz G S. Interactions of cytokines, growth factors, and proteases in acute and chronic wounds. *Wound Repair Regen* 1996; 4(4): 411-20.

Moseley R, Hilton J R, Waddington R J, Harding K G, Stephens P, Thomas D W. Comparison of oxidative stress biomarker profiles between acute and chronic wound environments. *Wound Repair Regen* 2004; 12(4): 419-29.

Sheldon A T (2005) Antiseptic "resistance": real or perceived threat? *Clin. Infect. Dis.* 40, 1650-1656.

Julia Bidder, MRSA, http://www.focus.de/gesundheit/arzt-klinik/klinik/tid-9019/mrsa-krank-durch-die-klinik_aid_262385.html. Feb. 26, 2010.

Bingham R. J.; Rudino-Pinera E.; Meenan N. A. G.; Schwarz-Linek U.; Turkenburg J. P.; Hook M.; Garman E. F.; Potts J. R. Proc. Natl. Acad. Sci. U.S.A. 2008, 105, 12254-12258.

O'Neill E.; Pozzi C.; Houston P.; Humphreys H.; Robinson D. A.; Loughman A.; Foster T. J.; O'Gara J. P. J. Bacteriol. 2008, 190, 3835-3850.

de Man et al., (1960) "A medium for Cultivation of Lactobacilli", J. Appl. Bact. 23(130-135)

The invention claimed is:

1. A method for coaggregating at least one pathogenic microorganism comprising:
providing a microorganism selected from the group consisting of *Lactobacillus* crispatus, *Lactobacillus* gasseri and *Lactobacillus fermentum* which is also selected from the group consisting of the following microorganisms which have been deposited with the German Collection for Microorganisms and Cell Cultures (DSMZ) under accession numbers DSM 25906, DSM 25907, DSM 25908, DSM 25909, DSM 25910, DSM 25911, DSM 25912, DSM 25913, DSM 25914, DSM 25915 and combinations thereof and contacting the microorganism with the least one pathogenic microorganism, wherein the microorganism selected from the group consisting of *Lactobacillus* crispatus, *Lactobacillus* gasseri and *Lactobacillus fermentum* which is also selected from the group consisting of microorganisms deposited with the DSMZ under accession numbers DSM 25906, DSM 25907, DSM 25908, DSM 25909, DSM 25910, DSM 25911, DSM 25912, DSM 25913, DSM 25914, DSM 25915 and combinations thereof coaggregates with said at least one pathogenic microorganism, wherein the pathogenic microorganism is selected from the group consisting of *Staphylococcus aureus*, *Pseudomonas aeruginosa* and combinations thereof.

2. The method of claim 1, wherein the microorganism selected from the group consisting of microorganisms deposited with the DSMZ under accession numbers DSM 25906, DSM 25907, DSM 25908, DSM 25909, DSM 25910, DSM 25911, DSM 25912, DSM 25913, DSM 25914, DSM 25915 and combinations thereof coaggregates with the at least one pathogenic microorganism even after a biological, chemical or physical treatment.

3. The method of claim 1 wherein the microorganism selected from the group consisting of microorganisms deposited with the DSMZ under accession numbers DSM 25906, DSM 25907, DSM 25908, DSM 25909, DSM 25910, DSM 25911, DSM 25912, DSM 25913, DSM 25914, DSM 25915 and combinations thereof coaggregates with the at least one pathogenic microorganism at a pH between approximately 3 and approximately 8.

4. The method of claim 1 wherein the microorganism selected from the group consisting of microorganisms deposited with the DSMZ under accession numbers DSM 25906, DSM 25907, DSM 25908, DSM 25909, DSM 25910, DSM 25911, DSM 25912, DSM 25913, DSM 25914, DSM 25915 and combinations thereof inhibits formation of a biofilm of the at least one pathogenic microorganism.

5. The method of claim 1, wherein said microorganism selected from the group consisting of microorganisms deposited with the DSMZ under accession numbers DSM 25906, DSM 25907, DSM 25908, DSM 25909, DSM 25910, DSM 25911, DSM 25912, DSM 25913, DSM 25914, DSM 25915 and combinations thereof is administered to a patient in need of treatment or at risk of a skin disease selected from the group consisting of staphylococcal scalded skin syndrome, impetigo contagiosa, folliculitis superficialis, impetiginization, skin abscesses, furuncles, carbuncles, abscesses, phlegmons, dry skin, itching skin, reddened skin, irritated skin, oily skin, acne, diabetic foot ulcer, decubital ulcer, neurodermatitis, acute lymphadenitis, pilonidal cysts, pilonidal fistulas, pilonidal sinus, coccidial fistula, coccidial cysts, local infections of the skin and subcutaneous tissue, pyoderma, dermatitis purulenta, dermatitis septica, dermatitis suppurativa, dermatitis and eczema, atopic eczema, seborrheic eczema, diaper rash, allergic contact dermatitis, seborrheic dermatitis, exfoliative dermatitis, toxic contact dermatitis, lichen simplex chronicus, prurigo, pruritus, papulosquamous skin diseases, psoriasis, parapsoriasis, cicatricial alopecia, folliculitis decalvans, crural ulcers, skin injuries, scrapes, wounds after accidents or surgery.

6. The method of claim 5, wherein a composition comprising the microorganism selected from the group consisting of microorganisms deposited with the DSMZ under accession numbers DSM 25906, DSM 25907, DSM 25908, DSM 25909, DSM 25910, DSM 25911, DSM 25912, DSM 25913, DSM 25914, DSM 25915 and combinations thereof is provided prophylactically or curatively.

7. The method of claim 5, wherein a composition comprising the microorganism selected from the group consisting of microorganisms deposited with the DSMZ under accession numbers DSM 25906, DSM 25907, DSM 25908, DSM 25909, DSM 25910, DSM 25911, DSM 25912, DSM 25913, DSM 25914, DSM 25915 and combinations thereof is applied topically.

8. The method of claim 5, wherein the microorganism selected from the group consisting of microorganisms deposited with the DSMZ under accession numbers DSM 25906, DSM 25907, DSM 25908, DSM 25909, DSM 25910, DSM 25911, DSM 25912, DSM 25913, DSM 25914, DSM 25915 and combinations thereof is in form of an antimicrobial additive and wound infections or chronic wounds are topically treated.

9. The method of claim 1, wherein said microorganism selected from the group consisting of microorganisms deposited with the DSMZ under accession numbers DSM 25906, DSM 25907, DSM 25908, DSM 25909, DSM 25910, DSM 25911, DSM 25912, DSM 25913, DSM 25914, DSM 25915 and combinations thereof is part of a cleaning agent or disinfectant and surfaces are treated with said cleaning agent or disinfectant.

10. The method of claim 1, wherein said microorganism selected from the group consisting of microorganisms deposited with the DSMZ under accession numbers DSM 25906, DSM 25907, DSM 25908, DSM 25909, DSM 25910, DSM 25911, DSM 25912, DSM 25913, DSM 25914, DSM 25915 and combinations thereof is administered to a patient in need of treatment or at risk of *Staphylococcus aureus* or *Pseudomonas aeruginosa* infection.

11. The method of claim 1, wherein the patient is a commercial animal or a household pet.

* * * * *